(12) United States Patent
Ober et al.

(10) Patent No.: US 7,824,839 B2
(45) Date of Patent: Nov. 2, 2010

(54) PHOTOACID GENERATOR COMPOUNDS AND COMPOSITIONS

(75) Inventors: Christopher K. Ober, Ithaca, NY (US); Yi Yi, Urbana, IL (US); Ramakrishnan Ayothi, San Jose, CA (US)

(73) Assignee: Cornell Research Foundation, Inc., Ithaca, NY (US)

( * ) Notice: Subject to any disclaimer, the term of this patent is extended or adjusted under 35 U.S.C. 154(b) by 130 days.

(21) Appl. No.: 12/255,266

(22) Filed: Oct. 21, 2008

(65) Prior Publication Data

US 2009/0136868 A1   May 28, 2009

Related U.S. Application Data

(63) Continuation of application No. PCT/US2007/009714, filed on Apr. 23, 2007.

(60) Provisional application No. 60/793,988, filed on Apr. 21, 2006.

(51) Int. Cl.
G03F 7/00 (2006.01)
G03F 7/004 (2006.01)
G03F 7/029 (2006.01)
C07C 303/00 (2006.01)
C07D 307/00 (2006.01)

(52) U.S. Cl. .................... 430/270.1; 430/311; 430/330; 430/913; 430/905; 549/295; 549/323; 558/57

(58) Field of Classification Search .............. 430/270.1, 430/311, 330, 913, 905; 549/323, 295; 558/57
See application file for complete search history.

(56) References Cited

U.S. PATENT DOCUMENTS

| | | | |
|---|---|---|---|
| 5,468,902 A | 11/1995 | Castellanos et al. |
| 5,514,728 A | 5/1996 | Lamanna et al. |
| 5,554,664 A | 9/1996 | Lamanna et al. |
| 5,565,500 A | 10/1996 | Meier et al. |
| 5,710,320 A | 1/1998 | Vogel et al. |
| 5,981,140 A | 11/1999 | Sato et al. |
| 6,200,728 B1 | 3/2001 | Cameron et al. |
| 6,485,883 B2 | 11/2002 | Kodama et al. |
| 6,692,893 B2 | 2/2004 | Ohsawa et al. |

(Continued)

FOREIGN PATENT DOCUMENTS

CN        1066446        11/1992

(Continued)

OTHER PUBLICATIONS

"U.S. Appl. No. 11/080,658, Non-Final Office Action mailed Jul. 24, 2007", 13 pgs.

(Continued)

*Primary Examiner*—Amanda C. Walke
(74) *Attorney, Agent, or Firm*—Schwegman, Lundberg & Woessner, P.A.

(57) ABSTRACT

The invention provides various ionic and non-ionic photoacid generator compounds. Photoresist compositions that include the novel ionic and non-ionic photoacid generator compounds are also provided. The invention further provides methods of making and using the photoacid generator compounds and photoresist compositions disclosed herein. The compounds and compositions are useful as photoactive components in chemically amplified resist compositions for various microfabrication applications.

14 Claims, 3 Drawing Sheets

PAG Sensitivity at 254 nm poly(HOST-co-St-co-t-BA): 6 wt%, ~ 150 nm;
PAG: 5.3 μmol; PAB/PEB: 115 °C/60s; 0.13 N TMAH/5s

U.S. PATENT DOCUMENTS

| | | | |
|---|---|---|---|
| 6,749,987 | B2 | 6/2004 | Kodama et al. |
| 6,908,722 | B2 | 6/2005 | Ebata et al. |
| 6,924,323 | B2 | 8/2005 | Ishihara et al. |
| 6,929,896 | B2 | 8/2005 | Yamato et al. |
| 6,949,329 | B2 | 9/2005 | Endo et al. |
| 7,105,267 | B2 | 9/2006 | Hatakeyama et al. |
| 7,122,291 | B2 | 10/2006 | Padmanaban et al. |
| 7,163,776 | B2 | 1/2007 | Sasaki et al. |
| 7,288,359 | B2 * | 10/2007 | Iwasawa et al. .......... 430/270.1 |
| 7,393,627 | B2 | 7/2008 | Ober et al. |
| 7,618,765 | B2 * | 11/2009 | Nishi et al. .............. 430/270.1 |
| 2002/0102491 | A1 | 8/2002 | Kodama et al. |
| 2002/0197558 | A1 | 12/2002 | Ferreira et al. |
| 2003/0027061 | A1 | 2/2003 | Cameron et al. |
| 2003/0113658 | A1 | 6/2003 | Ebata et al. |
| 2003/0170561 | A1 | 9/2003 | Iwasawa et al. |
| 2003/0180596 | A1 | 9/2003 | Yoshimura et al. |
| 2003/0219679 | A1 | 11/2003 | Sasaki et al. |
| 2004/0033440 | A1 | 2/2004 | Maeda et al. |
| 2004/0087690 | A1 | 5/2004 | Lamanna et al. |
| 2005/0158655 | A1 * | 7/2005 | Lamanna et al. ......... 430/270.1 |
| 2005/0208420 | A1 | 9/2005 | Ober et al. |
| 2007/0148592 | A1 * | 6/2007 | Wada et al. .............. 430/270.1 |
| 2008/0227032 | A1 | 9/2008 | Ober et al. |
| 2009/0042124 | A1 * | 2/2009 | Kamimura et al. ....... 430/270.1 |
| 2009/0075202 | A1 * | 3/2009 | Kodama et al. .......... 430/285.1 |
| 2009/0258315 | A1 | 10/2009 | Ober et al. |

FOREIGN PATENT DOCUMENTS

| | | |
|---|---|---|
| DE | 295421 | 10/1991 |
| EP | 1270553 A2 | 1/2003 |
| JP | 2001-159812 | 6/2001 |
| WO | WO-02/18332 A1 | 3/2002 |
| WO | WO-2007/124092 A2 | 11/2007 |

OTHER PUBLICATIONS

"U.S. Appl. No. 11/080,658, Response filed Nov. 26, 2007 to Non-Final Office Action mailed Jul. 24, 2007", 8 pgs.

"U.S. Appl. No. 11/080,658, Non-Final Office Action mailed Dec. 28, 2006", 6 pgs.

"U.S. Appl. No. 11/080,658, Notice of Allowance mailed Feb. 26, 2008", 6 pgs.

"U.S. Appl. No. 11/080,658, Response filed Apr. 30, 2007 to Non-Final Office Action mailed Dec. 28, 2006", 18 pgs.

"U.S. Appl. No. 12/129,507, Non-Final Office Action mailed Dec. 12, 2008", 10 pgs.

"International Application Serial No. PCT/U805/08678, International Search Report mailed Mar. 3, 2006", 2 pgs.

"International Application Serial No. PCT/U805/08678, Written Opinion mailed Mar. 3, 2006", 4 pgs.

"International Application Serial No. PCT/US07/09714, International Search Report mailed Oct. 15, 2007", 3 pgs.

"International Application Serial No. PCT/US07/09714, Written Opinion mailed Oct. 15, 2007", 6 pgs.

Blotny, G., "A New, Mild Preparation of Sulfonyl Chlorides", *Tetrahedron Letters*, 44, (2003), 1499-1501.

Crivello, J. V., et al., "Diaryliodonium Salts. A New Class of Photoinitiators for Cationic Polymerization", *Macromolecules*, 10(6), (Nov.-Dec. 1977), 1307-1315.

Crivello, J. V., et al., "Synthesis and Characterization of Second-Generation Dialkylphenacylsulfonium Salt Photoinitiators", *Macromolecules*, 33(3), (2000), 825-832.

De Vleeschauwer, M., et al., "Remarkably Mild and Simple Preparations of Sulfinates, Sulfonyl Chlorides and Sulfonamides From Thioanisoles", *Synlett*, (Apr. 1997), 375-377.

Ding, Y., et al., "$LnCl_3$(cat.)/En Promoted Hydroperfluoroalkylation of α β—Unsaturated Esters With Perfluoroalkyl Iodides", *Tetrahedron Letters*, 33(52), (1992), 8119-8120.

Feiring, A. E., et al., "Aromatic Monomers With Pendant Fluoroalkylsulfonate and Sulfonimide Groups", *Journal of Fluorine Chemistry*, 105, (2000), 129-135.

Feiring, A. E., "Reaction of Perfluoroalkylk Iodides With Electron Donor Nucleophiles. Addition of Perfluoroalkyl Iodides to Olefins Initiated by Electron Transfer", *Journal of Organic Chemistry*, 50(18), (1985), 3269-3274.

Gisler, M., et al., "Neue Methods zur Phasentransfer-Katalysierten Sulfodechlorierung von 1-Chlor-2,4-dinitrobenzol [New Method for the Phase Transfer-Catalyzed Sulfodechlorination of 1-chloro-2,4-dinitrobenzene]", *Angewandte Chemie*, 93(2), (Abstract Only), (1981), 1 pg.

Gisler, M., et al., "Novel Method for the Phase-Transfer Catalyzed Sulfodechlorination of 1-Chloro-2,4-dinitrobenzene", *Angew. Chem. Int. Ed. Engl.*, 20(2), (1981), 203-204.

Guo, X.-C., et al., "The First Example of Addition Reactions of Sterically Hindered Terminal Olefins, alpha-Substituted Styrenes, With Perfluoroalkyl Iodides Initiated by Sodium Dithionite", *Journal of Fluorine Chemistry*, 93, (1999), 81-86.

Hasan, A., et al., "Photolabile Protecting Groups for Nucleosides: Synthesis and Photodeprotection Rates", *Tetrahedron*, 53(12), (1997), 4247-4267.

Houlihan, F. M., et al., "Design, Synthesis, Characterization, and Use of All-Organic Nonionic Photogenerators of Acid", *Chemistry of Materials*, 3(3), (1991), 462-471.

Hu, C.-M., et al., "Cobaloxime-Catalyzed Hydroperfluoroalkylation of Electron-Deficient Alkenes With Perfluoroalkyl Halides: Reaction and Mechanism", *Journal of Organic Chemistry*, 57(12), (1992), 3339-3342.

Hu, C.-M., et al., "Reaction of Perfluoroalkanesulfinates With Allyl and Propargy Halides. A Convenient Synthesis of 3-(Perfluoroalky)prop-1-enes and 3-(Perfluoroalkyl)allenes", *Journal of Organic Chemistry*, 56(8), (1991), 2801-2804.

Hu, C.-M., et al., "Redox-Initiated Per(poly)fluoroalkylation of Olefins by Per(poly)fluoroalkyl Chlorides", *Journal of Organic Chemistry*, 56(22), (1991), 6348-6351.

Imazeki, S., et al., "Facile Method for the Preparation of Triarylsulfonium Bromides Using Grignard Reagents and Chlorotrimethylsilane as an Activator", *Synthesis*, 10, (2004), 1648-1654.

Iwashima, C., et al., "Synthesis of i- and g-Line Sensitive Photoacid Generators and Their Application to Photopolymer Systems", *Journal of Photopolymer Science and Technology*, 16(1), (2003), 91-96.

Long, Z.-Y., et al., "The Activation of Carbon-Chlorine Bonds in Per- and Polyfluoroalkyl Chlorides: DMSO-Induced Hydroperfluoroalkylation of Alkenes and Alkynes with Sodium Dithionite", *Journal of Organic Chemistry*, 64(13), (1999), 4775-4782.

Lu, X., et al., "Samarium Diiodide Initiated Addition Reaction of Fluoroalkyl Iodides to Olefins", *Tetradedron Letters*, 29(40), (1988), 5129-5130.

Okamura, H., et al., "Evaluation of Quantum Yields for Decomposition of I-Line Sensitive Photoacid Generators", *Journal of Photopolymer Science and Technology*, 16(5), (2003), 701-706.

Okamura, H., et al., "I-Line Sensitive Photoacid Generators and Their Use for Photocrosslinking of Polysilane/diepoxyfluorene Blend", *Journal of Photopolymer Science and Technology*, 16(1), (2003), 87-90.

Richard, J. P., et al., "The Effect of β-Fluorine Substituents on the Rate and Equilibrium Constants for the Reactions of α-Substituted 4-Methoxybenzyl Carbocations and on the Reactivity of a Simple Quinone Methide", *Journal of American Chemical Society*, 112(26), (1990), 9513-9519.

Serafinowski, P. J., et al., "Novel Photoacid Generators for Photodirected Oligonucleotide Synthesis", *Journal of the American Chemical Society*, 125, (2003), 962-965.

Shirai, M., et al., "Development of Novel Photosensitive Polymer Systems Using Photoacid and Photobase Generators", *Journal of Photopolymer Science and Technology*, 15(5), (2002), 715-730.

Shirai, M., et al., "Photoacid and Photobase Generators: Chemistry and Applications to Polymeric Materials", *Progress in Polymer Science*, 21(1), (1996), 1-45.

Willenbring, R. J., et al., "New Pentafluorothio(SF$_5$) Alkylsulfonic Acids", *Canadian Journal of Chemistry*, 67, (1989), 2037-2040.

Zhao, Z., "Synthesis of Sodium Picrylsulfonate", *Huaxue Shiji*, 8(5), (Abstract Only), (1986), 1 pg.

Zou, X., et al., "Synthesis of Polyfluoroalkyl-γ-lactones From Polyfluoroalkyl Halides and 4-pentenoic Acids", *Tetrahedron*, 59, (2003), 2555-2560.

* cited by examiner

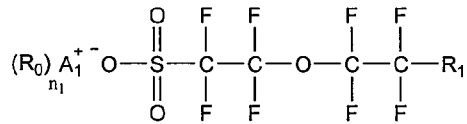

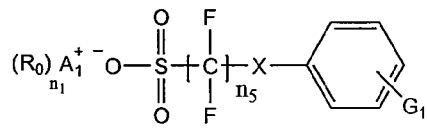

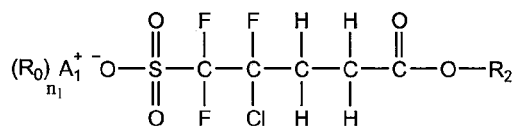

$R_1$ = phenyl, $COCH_2COC(CH_3)_3$
$R_2$ = aryl, aliphatic or cycloaliphatic groups

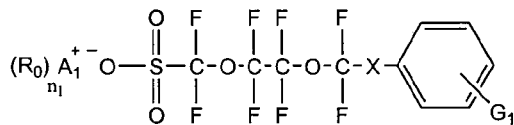

$n_5$ = 1-4; X = S, $CH_2$
$G_1$ = H, Br, CN, $OCH_3$, $COO^-$, $NO_2$, $OCOCH_3$

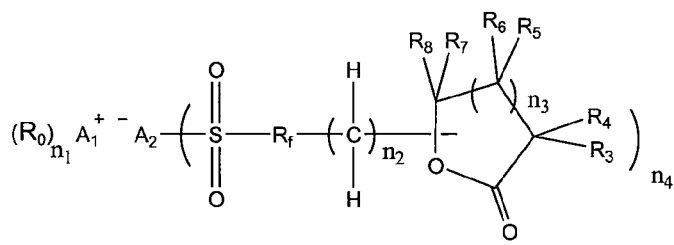

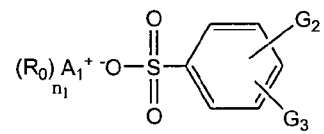

$R_f = CF_2CF_2OCF_2CF_2$ or $(CF_2)_m$, m = 1-6.
The fluorinated group is connected to the lactone group at any postion on the ring;
$R_{3-8}$ = H, aryl, alkyl, cycloalkyl groups, or the group that includes $R_f$;
$n_2$ = 0-5, $n_3$ = 1 or 2.
$A_2$ = O, $n_4$=1; $A_2$= N, $n_4$ = 2.

$G_2$, $G_3$ = H, F, Br, $OCH_3$, $COO^-$, CN, $OCOCH_3$, $CF_3$, $NO_2$ $A_1$ = I, $n_1$ = 2; $A_1$ = S, $n_1$ = 3.
$R_0$ = the same or different aryl, aliphatic or cycloaliphatic groups with or without substituents.

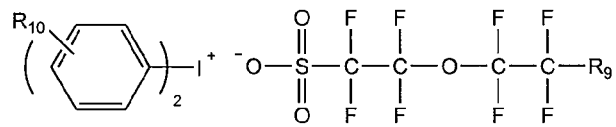

$R_9$ = aryl, alkyl, cycloalkyl, alkoxyl, cycloalkoxyl, oxoalkyl, oxocycloalkyl, cycloether, norbornyl, admantyl, heterocycle, or heterocycle-substituted alkyl.
$R_{10}$ = H, alkyl (e.g. $t$-butyl) or ester group.

PHOTOACID GENERATOR COMPOUNDS AND COMPOSITIONS

RELATED APPLICATIONS

This application is a continuation under 35 U.S.C. 111(a) of International Application No. PCT/US2007/009714, filed Apr. 23, 2007 and published in English as WO 2007/124092 on Nov. 1, 2007, which claims priority from U.S. Provisional Application No. 60/793,988, filed Apr. 21, 2006, which applications and publication are incorporated herein by reference.

BACKGROUND OF THE INVENTION

Several acid-catalyzed chemically amplified resist compositions have been developed. Chemically amplified resist compositions generally include a photosensitive acid ("photoacid") generator (PAG) and an acid sensitive polymer (resist). Upon exposure to radiation (e.g., x-ray radiation, ultraviolet radiation), the photoacid generator, by producing a proton, creates a photo-generated catalyst (usually a strong acid) during the exposure to radiation. During a post-exposure bake (PEB), the acid may act as a catalyst for further reactions. For example, the acid generated may facilitate the deprotection or cross-linking in the photoresist. Generation of acid from the PAG does not necessarily require heat. However, many known chemically amplified resists require a post-exposure bake (PEB) to complete the reaction between the acid moiety and the acid labile component. Chemical amplification type resist materials include positive working materials that leave unexposed material with the exposed areas removed and negative working materials that leave exposed areas with the unexposed areas removed.

Photoacid generators (PAGs) play a critical role in chemically amplified resist systems. Among the various classes of ionic and nonionic PAGs that have been developed, one of the most widely used classes is the perfluorinated onium salts. Recently, government action has rendered many of the most effective PAGs no longer commercially viable, including those based on perfluorooctyl sulfonates (PFOS). In addition to environmental concerns, the PFOS-based PAGs are a concern due to their fluorous self-assembly and their diffusion characteristics at smaller dimensions. Previous efforts to develop new PAGs have focused mainly on improving the photosensitive onium cation side to increase the quantum yield or to improve absorbance. The nature of the photoacid produced upon irradiation of the PAG is directly related to the anion of the ionic PAG. Difference in acid strength, boiling point, size, miscibility, and stability of the photoacid produced can affect parameters related to photoresist performance, such as deprotection (or cross-linking) efficiency, photospeed, post-exposure bake (PEB) sensitivity, post-exposure delay (PED) stability, resolution, standing waves, image profiles, and acid volatility. Because PFOS-based PAGs are being phased out and current commercial PAGs have significant drawbacks with respect to the previously mentioned properties, new PAGs that can help resolve these environmental and performance issue are needed.

SUMMARY OF THE INVENTION

One aspect of the present invention relates to the anionic component of ionic photoacid generators (PAGs). By designing new sulfonate anions, the homogeneous distribution of the PAG in a resist can be improved and appropriate mobility of the photogenerated acid can be obtained. At the same time, these PAGs with new sulfonate anions can favorably address environmental issues, including the need to reduce or eliminate the use of PFOSs.

To address environmental concerns related to the use of PFOS PAGs, sulfonic acids have been developed that contain fewer fluorinated carbons than typically found in PFOS. Perfluoro segments have been replaced with various functional groups that maintain the strong polarization of the acid (i.e., pKa), control the size, and aid film formation and compatibility with the matrix resin. In contrast to PFOS, the new PAGs with novel fluoro-organic sulfonate anions contain various functional groups that allow them to degrade by chemical or physical modes to produce relatively short fluorine containing molecules. These new PAGs are expected to be non-bioaccumalitive and environmentally friendly so there is less impact on the environment and on living organisms.

The present invention is also directed to a new approach to produce environmentally friendly photoacid generators (PAGs) having anions that comprise either short or no perfluoroalkyl chain (no-PFOS) attached to a variety of functional groups. The photoacid generators of the present invention can be formed from onium salts and various derivative compounds, for example, as illustrated in formula I:

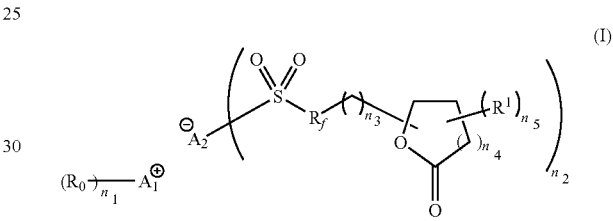

wherein
  $A_1$ is I or S;
  $n_1$ is 2 when $A_1$ is I, and $n_1$ is 3 when $A_1$ is S;
  each $R_0$ is independently alkyl, cycloalkyl, heterocycle, aryl, or heteroaryl, each optionally substituted with one to about five substituents;
  $A_2$ is O or N;
  $n_2$ is 1 when $A_2$ is O and $n_2$ is 2 when $A_2$ is N;
  $R_f$ is a diradical carbon chain comprising one to about 20 carbon atoms wherein the chain is optionally interrupted by one to five oxygen atoms, and each carbon atom is substituted with zero to two halo groups, or $R_f$ is a direct bond;
  each $R_1$ is independently H, alkyl, cycloalkyl, heterocycle, aryl, or heteroaryl;
  $n_3$ is 0 to about 10;
  $n_4$ is 1 or 2;
  $n_5$ is 0 to 7; and
  any aryl or heteroaryl is optionally substituted with one to five halo, $(C_1-C_6)$alkyl, alkoxy, acyl, alkoxycarbonyl, alkoxyacyl, acyloxy, trifluoromethyl, trifluoromethoxy, hydroxy, cyano, carboxy, nitro, or $-N(R^2)_2$ groups;
  any alkyl, cycloalkyl, heterocycle, aryl, or heteroaryl is optionally substituted with one to five halo, $(C_1-C_6)$alkyl, alkoxy, acyl, alkoxyacyl, acyloxy, trifluoromethyl, trifluoromethoxy, hydroxy, cyano, carboxy, nitro, $-N(R^2)_2$, or oxo groups; and
  each $R^2$ is independently H, alkyl, aryl, acyl, or aroyl.

Specific values for $R_0$ include aryl and heteroaryl, more specifically, phenyl, or pyridyl.

The diradical carbon chain comprising one to about 20 carbon atoms can have about 2 to about 15 carbon atoms, or about 4 to about 10 carbon atoms in the chain, excluding heteroatom interruptions. In various embodiments, $R_f$ is substituted with two fluoro groups. In other embodiments, $R_f$ is a direct bond. In yet other embodiments, $R_f$ includes at least four fluoro groups, or at least eight fluoro groups. $R_f$ can also be —$(CF_2)_n$— wherein n is 1, 2, 3, 4, 5, 6, 7, or 8, —$C(CF_3)_2$—, —$(CF_2)$—O—$(CF_2)_2$—O—$(CF_2)$—, —$(CF_2)_2$—O—$(CF_2)_2$—, or a direct bond.

In various embodiments, $n_3$ is 1. In certain embodiments, $n_4$ is 1. In some embodiments, $n_5$ is 0, or $n_5$ is 1 and $R^1$ is ($C_1$-$C_8$)alkyl. The variable $n_5$ can also be 1 and $R^1$ can be methyl, in either the R or S stereoisomeric conformation.

The present invention is also directed to a new approach to produce environmentally friendly photoacid generators (PAGs) that are non-ionic and that comprise either short or no perfluoroalkyl chains (no-PFOS) attached to a variety of functional groups. The photoacid generators of the present invention are formed from various chromophoric moieties and organic or partially fluoroorganic moieties, and their derivatives, for example, as illustrated in formula II. Accordingly, the invention provides PAGs, including compounds of formula II:

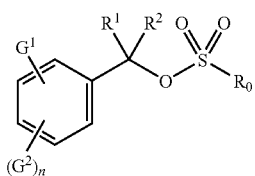

(II)

wherein $R_0$ is alkyl, cycloalkyl, heterocycle, aryl, or heteroaryl, optionally substituted with one to about five substituents;

$R_1$ and $R_2$ are each independently H, alkyl, cycloalkyl, heterocycle, aryl, or heteroaryl;

$G^1$ is H, halo, hydroxy, nitro, cyano, trifluoromethyl, or trifluoromethoxy;

each $G^2$ is independently alkyl, cycloalkyl, heterocycle, aryl, heteroaryl, halo, alkoxy, acyl, alkoxycarbonyl, alkoxyacyl, acyloxy, trifluoromethyl, trifluoromethoxy, hydroxy, cyano, carboxy, nitro, or —$N(R^2)_2$ wherein each $R^2$ is independently H, alkyl, aryl, acyl, or aroyl;

n is 0, 1, 2, 3, or 4; and any alkyl, cycloalkyl, heterocycle, aryl, or heteroaryl is optionally substituted with one to five halo, ($C_1$-$C_6$)alkyl, alkoxy, acyl, alkoxyacyl, acyloxy, trifluoromethyl, trifluoromethoxy, hydroxy, cyano, carboxy, nitro, —$N(R^2)_2$, or oxo groups.

The variable $R_0$ can be optionally substituted aryl. $R_0$ can also be optionally substituted phenyl. For example, the aryl (or phenyl) can be substituted with one or more substituents as described in the Detailed Description below.

In various embodiments, $R^2$ can be H. In certain embodiments, $R^1$ is not H. In some embodiments, $G^1$ can be nitro. In such embodiments, $G^1$ can be nitro at the ortho position, or alternatively, the substitution can be meta or para to the chain attachment.

The variable $G^2$ can be F or —$CF_3$.

The compound of formula II can be substituted with at least 2 fluoro groups, preferably 3-6 fluoro groups. In some embodiments, the compound is substituted with at least 3 fluoro groups, preferably 4-6 fluoro groups.

Thus, the invention also provides a compound of formula III:

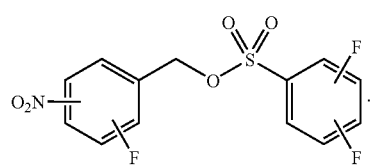

(III)

Additionally, a compound of formula III can be the compound

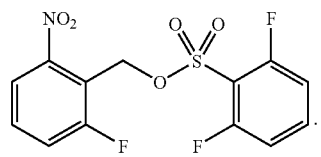

The invention also provides methods of preparing the compounds and compositions described herein.

Each of the compounds of the invention can be used to prepare a chemical amplification type resist composition that includes the photoacid generator. The chemical amplification type resist composition can include a resin that changes its solubility in an alkaline developer when contacted with an acid. Other compounds can be added to the composition, for example, compounds capable of generating an acid upon exposure to radiation other than a compound of formula I or II. The chemical amplification type resist composition can further include a basic compound.

Finally, the invention provides a method to form a pattern comprising:

a) applying a resist composition that includes a compound of formula I or II onto a substrate to provide a substrate with a coating;

b) heat treating the coating and exposing the coating to high energy radiation or electron beam through a photo-mask; and c) optionally heat treating the exposed coating and developing the coating with a developer.

The compounds and onium salts of the present invention provide a photoacid generator for chemical amplification type resist compositions comprising the compounds or onium salts described above.

In one embodiment, the invention provides: a chemical amplification type resist composition comprising (i) a resin that changes its solubility in an alkaline developer under the action of an acid, and (ii) the aforementioned photoacid generator (PAG) that generates an acid upon exposure to radiation.

In another embodiment, the invention provides: a chemical amplification type resist composition comprising (i) a resin that changes its solubility in an alkaline developer under the action of an acid, (ii) the aforementioned photoacid generator (PAG) that generates an acid upon exposure to radiation, and (iii) a compound capable of generating an acid upon exposure to radiation, other than component (ii). The resist composition may further include (iv) a basic compound and/or (v) a carboxyl group-containing compound.

Additionally, the present invention provides a process for forming a pattern, including applying a resist composition described herein onto a substrate to form a coating; heat treating the coating and exposing the coating to high energy or electron beam through a photo-mask; optionally heat treating the exposed coating, and developing the coating with a developer.

BRIEF DESCRIPTION OF THE DRAWINGS

FIG. 2 illustrates general structures of ionic PAGs, according to various embodiments. The values listed for the variables in FIG. 2 are representative of certain embodiments; other embodiments may include other substituents as defined herein.

DETAILED DESCRIPTION

Figure 1:
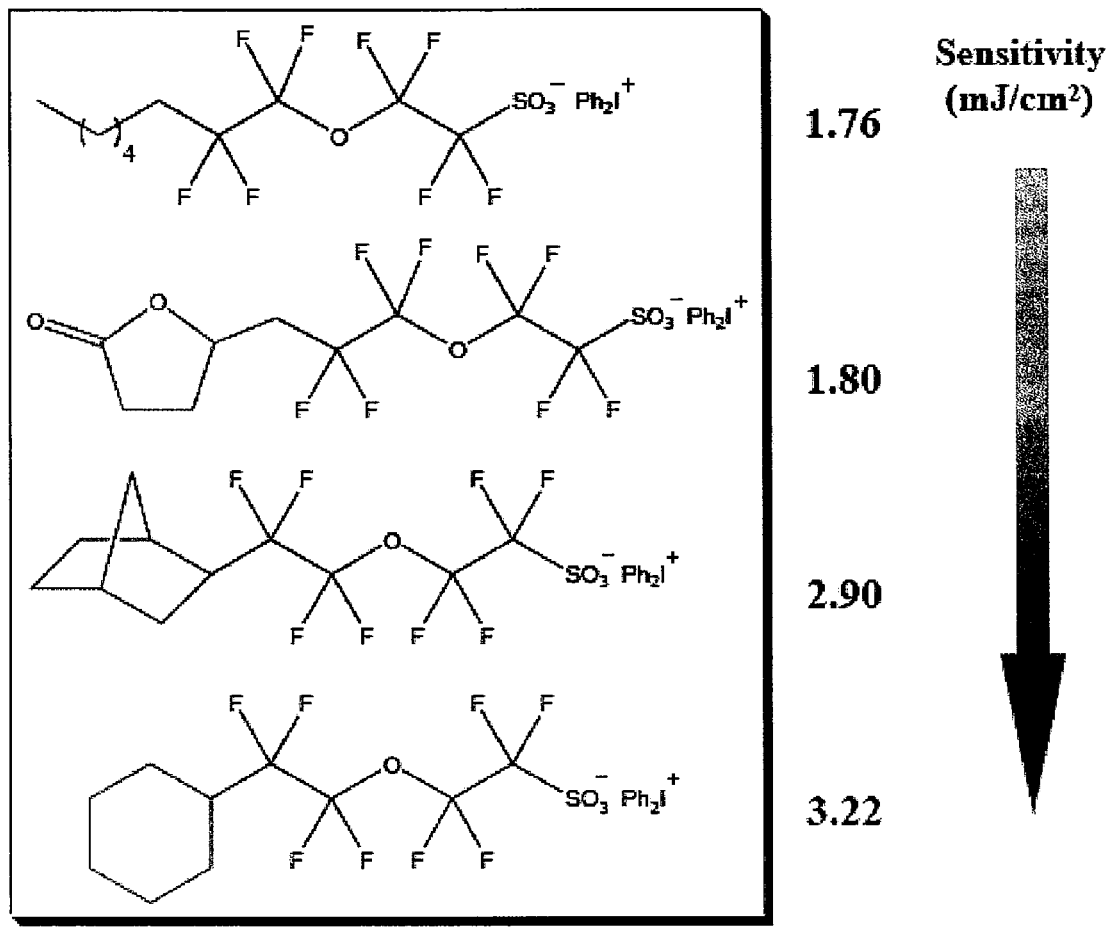
FIG. 1 illustrates the sensitivity of various photoacid generators at 254 nm.

As used herein, the following terms and expressions have the indicated meanings. It will be appreciated that the compounds of the present invention can contain asymmetrically substituted carbon atoms, and can be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomeric form is specifically indicated.

"Stable compound" and "stable structure" are meant to indicate a compound that is sufficiently robust to survive isolation to a useful degree of purity from a reaction mixture, and formulation into an efficacious therapeutic agent. Only stable compounds are contemplated by and employed in the present invention.

"Substituted" is intended to indicate that one or more (e.g., 1, 2, 3, 4, or 5; preferably 1, 2, or 3; and more preferably 1 or 2) hydrogen atoms on the atom indicated in the expression using "substituted" is replaced with a selection from the indicated group(s), provided that the indicated atom's normal valency is not exceeded, and that the substitution results in a stable compound. Suitable indicated groups (referred to as "substituents") include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Alternatively, the suitable indicated groups can include, e.g., —X, —R, —O⁻, —OR, —SR, —S⁻, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR, —S(=O)$_2$O⁻, —S(=O)$_2$OH, —S(=O)$_2$R, —OS(=O)$_2$OR, —S(=O)$_2$NR, —S(=O)R, —OP(=O)(OR)$_2$, —P(=O)(OR)$_2$, —P(=O)(O⁻)$_2$, —P(=O)(OH)$_2$, —C(=O)R, —C(=O)X, —C(S)R, —C(O)OR, —C(O)O⁻, —C(S)OR, —C(O)SR, —C(S)SR, —C(O)NRR, —C(S)NRR, —C(NR) NRR, where each X is independently a halogen: F, Cl, Br, or I; and each R is independently H, alkyl, aryl, heterocycle, protecting group or prodrug moiety. When a substituent is a keto (i.e., =O) or thioxo (i.e., =S) group, then 2 hydrogens on the atom are replaced. One or more of the aforementioned substituents can also be excluded from a compound or formula of the invention.

One diastereomer may display superior activity compared with the other. When required, separation of the racemic material can be achieved by high pressure liquid chromatography (HPLC) using a chiral column or by a resolution using a resolving agent such as camphonic chloride as in Thomas J. Tucker, et al., J. Med. Chem. 1994 37, 2437-2444. A chiral compound may also be directly synthesized using a chiral catalyst or a chiral ligand, e.g. Mark A. Huffman, et al., J. Org. Chem. 1995, 60, 1590-1594.

The term "alkyl" refers to a monoradical branched or unbranched saturated hydrocarbon chain preferably having from 1 to 10 carbon atoms, preferably 1 to 6 carbon atoms, and more preferably from 1 to 4 carbon atoms. Examples are methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH (CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$) CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH (CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$) CH$_2$CH$_2$CH$_2$CH$_3$), 3-hexyl (—CH(CH$_2$CH$_3$) (CH$_2$CH$_2$CH$_3$)), 2-methyl-2-pentyl (—C(CH$_3$)$_2$ CH$_2$CH$_2$CH$_3$), 3-methyl-2-pentyl (—CH(CH$_3$)CH(CH$_3$) CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C (CH$_3$)$_2$CH(CH$_3$)$_2$), 3,3-dimethyl-2-butyl (—CH(CH$_3$)C (CH$_3$)$_3$. The alkyl can be unsubstituted or substituted.

The term "alkenyl" refers to a monoradical branched or unbranched partially unsaturated hydrocarbon chain (i.e. a carbon-carbon, sp$^2$ double bond) preferably having from 2 to 10 carbon atoms, preferably 2 to 6 carbon atoms, and more preferably from 2 to 4 carbon atoms. Examples include, but are not limited to, ethylene or vinyl (—CH=CH$_2$), allyl (—CH$_2$CH=CH$_2$), cyclopentenyl (—C$_5$H$_7$), and 5-hexenyl (—CH$_2$CH$_2$CH$_2$CH$_2$CH=CH$_2$). The alkenyl can be unsubstituted or substituted.

The term "alkynyl" refers to a monoradical branched or unbranched hydrocarbon chain, having a point of complete unsaturation (i.e. a carbon-carbon, sp triple bond), preferably having from 2 to 10 carbon atoms, preferably 2 to 6 carbon atoms, and more preferably from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, and the like. The alkynyl can be unsubstituted or substituted.

"Alkylene" refers to a saturated, branched or straight chain hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene (—CH$_2$—) 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like. The alkynyl can be unsubstituted or substituted.

"Alkenylene" refers to an unsaturated, branched or straight chain hydrocarbon radical of 2-18 carbon atoms, and having two monovalent radical centers derived by the removal of two hydrogen atoms from the same or two different carbon atoms of a parent alkene. Typical alkenylene radicals include, but are not limited to, 1,2-ethylene (—CH═CH—). The alkenylene can be unsubstituted or substituted.

"Alkynylene" refers to an unsaturated, branched or straight chain hydrocarbon radical of 2-18 carbon atoms, and having two monovalent radical centers derived by the removal of two hydrogen atoms from the same or two different carbon atoms of a parent alkyne. Typical alkynylene radicals include, but are not limited to, acetylene (—C≡C—), propargyl (—CH$_2$C≡C—), and 4-pentynyl (—CH$_2$CH$_2$CH$_2$C≡CH—). The alkynylene can be unsubstituted or substituted.

The term "alkoxy" refers to the groups alkyl-O—, where alkyl is defined herein. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

The term "aryl" refers to an unsaturated aromatic carbocyclic group of from 6 to 12 carbon atoms having a single ring (e.g., phenyl) or multiple condensed (fused) rings, wherein at least one ring is aromatic (e.g., naphthyl, dihydrophenanthrenyl, fluorenyl, or anthryl). The aryl can be unsubstituted or substituted.

The term "cycloalkyl" refers to cyclic alkyl groups of from 3 to 10 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like. The cycloalkyl can be unsubstituted or substituted.

The term "halo" refers to fluoro, chloro, bromo, and iodo. Similarly, the term "halogen" refers to fluorine, chlorine, bromine, and iodine.

"Haloalkyl" refers to alkyl as defined herein substituted by 1-4 halo groups as defined herein, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, and the like.

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted, for example, with one or more, and in particular one to three, substituents, selected from alkyl, alkenyl, alkynyl, alkoxy, halo, haloalkyl, hydroxy, hydroxyalkyl, aryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl and cyano. Examples of heteroaryl groups include, but are not limited to, 2H-pyrrolyl, 3H-indolyl, 4H-quinolizinyl, 4nH-carbazolyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group non-peroxide oxygen, sulfur, and N(Z) wherein Z is absent or is H, O, alkyl, phenyl or benzyl. In another embodiment heteroaryl denotes an ortho-fused bicyclic heterocycle of about eight to ten ring atoms derived therefrom, particularly a benz-derivative or one derived by fusing a propylene, or tetramethylene diradical thereto.

"Heterocycle" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S).

Examples of heterocycles include, by way of example and not limitation: pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" refers to a saturated, unsaturated or aromatic ring having 3 to 7 carbon atoms as a monocycle, 7 to 12 carbon atoms as a bicycle, and up to about 30 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl, adamantly, and naphthyl.

The terms "cycloalkylene", "carbocyclene", "arylene", "heterocyclene", and "heteroarylene" refer to diradicals of the parent group. For example, "arylene" refers to an aryl diradical, e.g., an aryl group that is bonded to two other groups or moieties.

The term "alkanoyl" refers to C(=O)R, wherein R is an alkyl group as previously defined.

The term "alkoxycarbonyl" refers to C(=O)OR, wherein R is an alkyl group as previously defined.

The term "amino" refers to $-NH_2$, and the term "alkylamino" refers to $-NR_2$, wherein at least one R is alkyl and the second R is alkyl or hydrogen. The term "acylamino" refers to RC(=O)NH—, wherein R is alkyl or aryl.

As to any of the above groups, which contain one or more substituents, it is understood, of course, that such groups do not contain any substitution or substitution patterns that are sterically impractical and/or synthetically non-feasible. In addition, the compounds of this invention include all stereochemical isomers arising from the substitution of these compounds.

As used herein, "contacting" refers to the act of touching, making contact, or of bringing to immediate or close proximity, including at the molecular level.

Resist Compositions

Upon use of a chemical amplification type positive-working resist compositions, a resist film is formed by dissolving a resin having acid labile groups as a binder and a compound capable of generating an acid upon exposure to radiation ("a photoacid generator") in a solvent, applying the resist solution onto a substrate by a variety of methods, and evaporating off the solvent optionally by heating. The resist film is then exposed to radiation, for example, deep UV radiation, through a mask of a predetermined pattern. This is optionally followed by post-exposure baking (PEB) for promoting acid-catalyzed reaction. The exposed resist film is developed with an aqueous alkaline developer for removing the exposed area of the resist film, obtaining a positive pattern profile. The substrate is then etched by any desired technique. Finally the remaining resist film is removed by dissolution in a remover solution or ashing, leaving the substrate having the desired pattern profile.

Chemical amplification type positive-working resist compositions adapted for KrF excimer lasers generally use a phenolic resin, for example, polyhydroxy-styrene, in which some or all of the hydrogen atoms of phenolic hydroxyl groups are protected with acid labile protective groups. Onium salts, such as iodonium salts and sulfonium salts having perfluorinated anions, are typically used as the photoacid generator. If desired, the resist compositions can contains one or more additives, for example, a dissolution inhibiting or promoting compound in the form of a carboxylic acid and/or phenol derivative having a molecular weight of up to about 3,000, in which some or all of the hydrogen atoms of carboxylic acid and/or phenolic hydroxyl groups are protected with acid labile groups, a carboxylic acid compound for improving dissolution characteristics, a basic compound for improving contrast, and a surfactant for improving coating characteristics.

Ionic photoacid generators, typically onium salts, can be advantageously used as the photoacid generator in chemical amplification type resist compositions, especially chemical amplification type positive-working resist compositions adapted for KrF excimer lasers. Ionic photoacid generators provide a high sensitivity and resolution and are free from storage instability.

A compound of formula I or II can be used as a photoacid generator in a resist material, especially chemical amplification type resist materials. The invention provides resist compositions comprising a compound of one of formulas I-II as the photoacid generator. The resist compositions may be either positive- or negative-working. The resist compositions of the invention include a variety of embodiments, including one or more of any of the following, in any combination:

1) a chemically amplified positive working resist composition comprising (A) a resin that changes its solubility in an alkaline developer under the action of an acid, (B) a photoacid generator comprising a compound of one of formulas I-II capable of generating an acid upon exposure to radiation, and (C) an organic solvent;

2) a chemically amplified positive working resist composition of 1) above further comprising (D) a photoacid generator capable of generating an acid upon exposure to radiation other than component (B);

3) a chemically amplified positive working resist composition of 1) or 2) further comprising (E) a basic compound;

4) a chemically amplified positive working resist composition of 1) to 3) further comprising (F) an organic acid derivative;

5) a chemically amplified positive working resist composition of 1) to 4) further comprising (G) a compound with a molecular weight of up to about 3,000 that changes its solubility in an alkaline developer under the action of an acid;

6) a chemically amplified negative working resist composition comprising (B) a photoacid generator comprising a compound of one of formulas I-II capable of generating an acid upon exposure to radiation, (H) an alkali-soluble resin, an acid crosslinking agent capable of forming a crosslinked structure under the action of an acid, and (C) an organic solvent;

7) a chemically amplified negative working resist composition of 6) further comprising (D) another photoacid generator;

8) a chemically amplified negative working resist composition of 6) or 7) further comprising (E) a basic compound; as well as 9) a chemically amplified negative working resist composition of 6), 7) or 8) further comprising (J) an alkali-soluble compound with a molecular weight of up to about 2,500, up to about 5,000, or up to about 10,000.

Additionally, the invention provides a process for forming a pattern, comprising the steps of applying a resist composition described above onto a substrate to form a coating; heat treating the coating and exposing the coating to high energy radiation (for example, with a wavelength of up to 300 nm) or electron beam through a photo-mask; optionally heat treating the exposed coating, and developing the coating with a developer.

Various components of the compositions of the invention include the following:

Component (A): Resin

Component (A) is a resin which changes its solubility in an alkaline developer solution under the action of an acid. It is preferably, though not limited thereto, an alkali-soluble resin having phenolic hydroxyl and/or carboxyl groups in which some or all of the phenolic hydroxyl and/or carboxyl groups are protected with acid-labile protective groups.

The alkali-soluble resins having phenolic hydroxyl and/or carboxyl groups include homopolymers and copolymers of p-hydroxystyrene, m-hydroxystyrene, α-methyl-p-hydroxystyrene, 4-hydroxy-2-methylstyrene, 4-hydroxy-3-methylstyrene, methacrylic acid, and acrylic acid. Also included are copolymers in which units free of alkali-soluble sites such as styrene, α-methylstyrene, acrylate, methacrylate, hydrogenated hydroxystyrene, maleic anhydride and maleimide are introduced in addition to the above-described units in such a proportion that the solubility in an alkaline developer is not be extremely reduced. Substituents on acrylates and methacrylates may be any substituent that does not undergo acidolysis. In one embodiment, the substituents are straight, branched or cyclic ($C_1$-$C_8$)alkyl groups and aromatic groups such as aryl groups, but not limited thereto. In other specific embodiments, the substituents can be methyl, ethyl, propyl (normal or iso), butyl (normal or iso), cyclohexyl, etc., or combinations thereof.

Non-limiting examples of alkali-soluble resins are given below. These polymers may also be used as the material from which the resin (A) (which changes its solubility in an alkaline developer under the action of an acid) is prepared. These polymers may also be used as the alkali-soluble resin that serves as component (H), described hereinbelow. Examples include poly(p-hydroxystyrene), poly(m-hydroxystyrene), poly(4-hydroxy-2-methylstyrene), poly(4-hydroxy-3-methylstyrene), poly(α-methyl-p-hydroxystyrene), partially hydrogenated p-hydroxystyrene copolymers, p-hydroxystyrene-α-methyl-p-hydroxystyrene copolymers, p-hydroxystyrene-α-methylstyrene copolymers, p-hydroxystyrene-styrene copolymers, p-hydroxystyrene-m-hydroxystyrene copolymers, p-hydroxystyrene-styrene copolymers, p-hydroxystyrene-acrylic acid copolymers, p-hydroxystyrene-methacrylic acid copolymers, p-hydroxystyrene-methyl methacrylate copolymers, p-hydroxystyrene-acrylic acid-methyl methacrylate copolymers, p-hydroxystyrene-methyl acrylate copolymers, p-hydroxy-styrene-methacrylic acid-methyl methacrylate copolymers, poly(methacrylic acid), poly(acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydroxystyrene-methacrylic acid-maleimide copolymers, as well as dendritic and hyperbranched polymers thereof, but are not limited to these combinations.

The alkali-soluble resins or polymers should preferably have a weight average molecular weight (Mw) of about 3,000 to about 100,000. Many polymers with Mw of less than about 3,000 do not perform well in heat resistance and film formation. Many polymers with Mw of more than about 100,000 give rise to problems with respect to dissolution in the resist solvent and developer. The polymer can have a dispersity (Mw/Mn) of up to about 3.5, and more preferably up to about 1.5. With a dispersity of more than about 3.5, resolution is sometimes lower than is desired. Although the preparation method is not critical, a poly(p-hydroxystyrene) or similar polymer with a low dispersity or narrow dispersion can be synthesized by controlled free radical or living anionic polymerization.

The resin (A) can be an alkali-soluble resin having hydroxyl or carboxyl groups, some of which are replaced by acid labile groups such that the solubility in an alkaline developer changes as a result of severing of the acid labile groups under the action of an acid generated by the photoacid generator upon exposure to radiation.

In the chemical amplification type resist composition, an appropriate amount of (B) the photoacid generator comprising an a compound of one of formulas I-II added is from about 0.5 part to about 20 parts by weight, and typically from about 1 to about 10 parts by weight, per 100 parts by weight of the solids in the composition. The photoacid generators may be used alone or as admixture of two or more types. The transmittance of the resist film can be controlled by using a photoacid generator having a low transmittance at the exposure wavelength and adjusting the amount of the photoacid generator added.

Component B: Photoacid Generator Compounds (PAGs)

Figure 3:
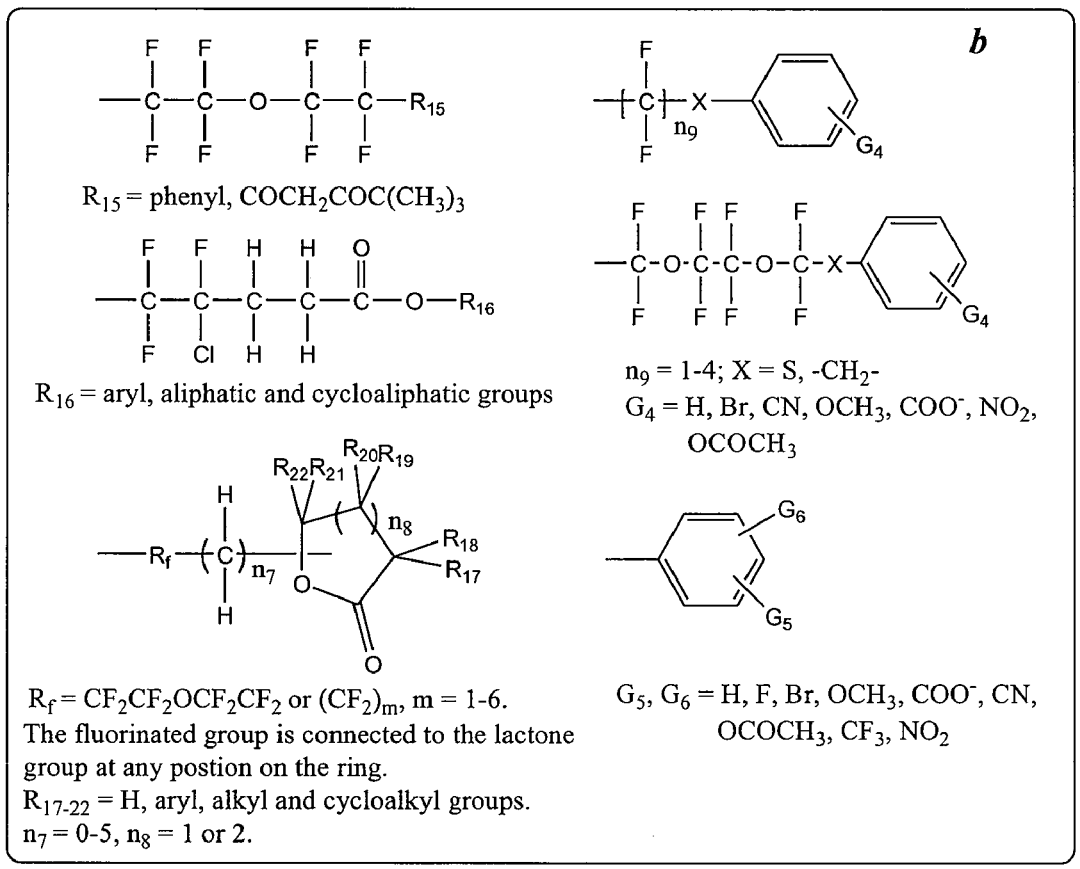
FIG. 3 illustrates general structures of nonionic PAGs wherein box a shows representative chromophore moieties and box b shows representative fluorinated groups. The values listed for the variables in FIG. 3 are representative of certain embodiments; other embodiments may include other substituents as defined herein.

The photoacid generator compound can be a compound of any one of formulas I-XI described herein. Several general and specific examples of useful PAGs are described and illustrated in the Examples section and in FIGS. 2 and 3.

Component (C): Solvent

Component (C) can be an organic solvent. Illustrative, non-limiting examples include butyl acetate, amyl acetate, cyclohexyl acetate, 3-methoxybutyl acetate, methyl ethyl ketone, methyl amyl ketone, cyclohexanone, cyclopentanone, 3-ethoxyethyl propionate, 3-ethoxymethyl propionate, 3-methoxymethyl propionate, methyl acetoacetate, ethyl acetoacetate, diacetone alcohol, methyl pyruvate, ethyl pyruvate, propylene glycol monomethyl ether, propylene glycol monoethyl ether, propylene glycol monomethyl ether propionate, propylene glycol monoethyl ether propionate, ethylene glycol monomethyl ether, ethylene glycol monoethyl ether, diethylene glycol monomethyl ether, diethylene glycol monoethyl ether, 3-methyl-3-methoxybutanol, N-methylpyrrolidone, dimethylsulfoxide, γ-butyrolactone, propylene glycol methyl ether acetate, propylene glycol ethyl ether acetate, propylene glycol propyl ether acetate, methyl lactate, ethyl lactate, propyl lactate, and tetramethylene sulfone. In one embodiment, the propylene glycol alkyl ether acetates and alkyl lactates are used in the compositions of the invention.

The alkyl groups of the propylene glycol alkyl ether acetates can be of 1 to about 4 carbon atoms, for example, methyl, ethyl and propyl. Propylene glycol alkyl ether acetates include 1,2- and 1,3-substituted derivatives and each includes up to about three isomers, depending on the combination of substituted positions, which may be used alone or in admixture. The alkyl groups of the alkyl lactates can be of 1 to 4 carbon atoms, for example, methyl, ethyl and propyl. These solvents may be used alone or in admixture. In one embodiment, a useful solvent system is a mixture of a propylene glycol alkyl ether acetate and an alkyl lactate. The mixing ratio of the propylene glycol alkyl ether acetate and the alkyl lactate can be a mixture of about 50 to about 99 parts by weight of the propylene glycol alkyl ether acetate with about 50 to about 1 part by weight of the alkyl lactate. The solvent mixture of the propylene glycol alkyl ether acetate and the alkyl lactate may further contain one or more other solvents.

Component (D): Additional Photoacid Generator Compound

In one embodiment, the resist composition further contains component (D), a compound capable of generating an acid upon exposure to high energy radiation, that is, a second photoacid generator other than the photoacid generator (B). The second photoacid generators include sulfonium salts and iodonium salts as well as sulfonyldiazomethane, N-sulfonyloxyimide, benzoinsulfonate, nitrobenzylsulfonate, sulfone, and glyoxime derivatives. They may be used alone or in admixture of two or more. Preferred component (D) photoacid generators used herein are sulfonium salts and iodonium salts.

In the resist composition comprising (B), a compound of one of formulas I-II, as the first photoacid generator, an appropriate amount of the second photoacid generator (D) is 0 to about 20 parts, and especially about 1 to about 10 parts by weight per 100 parts by weight of the solids in the composition. The second photoacid generators may be used alone or in admixture of two or more. The transmittance of the resist film can be controlled by using a (second) photoacid generator having a low transmittance at the exposure wavelength and adjusting the amount of the photoacid generator added.

Component (E): Base

The basic compound used as component (E) can be a compound capable of suppressing the rate of diffusion when the acid generated by the photoacid generator diffuses within the resist film. The inclusion of this type of basic compound holds down the rate of acid diffusion within the resist film, resulting in better resolution. In addition, it can suppress changes in sensitivity following exposure and can reduce substrate and environment dependence, as well as improve the exposure latitude and the pattern profile.

Examples of basic compounds include primary, secondary, and tertiary aliphatic amines, mixed amines, aromatic amines, heterocyclic amines, carboxyl group-bearing nitrogenous compounds, sulfonyl group-bearing nitrogenous compounds, hydroxyl group-bearing nitrogenous compounds, hydroxyphenyl group-bearing nitrogenous compounds, alcoholic nitrogenous compounds, amide derivatives, imide derivatives, and combinations thereof.

The basic compounds may be used alone or in admixture of two or more. The basic compound is preferably formulated in an amount of 0 to about 2 parts, and especially about 0.01 to about 1 part by weight, per 100 parts by weight of the solids in the resist composition. The use of more than about 2 parts of the basis compound can result in a low sensitivity.

Component (F)

Illustrative examples of the organic acid derivatives (F) include, but are not limited to, organic acid derivatives including 4-hydroxyphenylacetic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, salicylic acid, 4,4-bis(4'-hydroxy-phenyl) valeric acid, 4-tert-butoxyphenylacetic acid, 4-(4'-hydroxyphenyl)butyric acid, 3,4-dihydroxymandelic acid, 4-hydroxymandelic acid, and combinations thereof. In certain embodiments, salicylic acid and 4,4-bis(4'-hydroxyphenyl) valeric acid are employed. They may be used alone or in admixture of two or more.

In the resist composition comprising a compound of one of formulas I-II, the organic acid derivative can be formulated in an amount of up to about 5 parts, and especially up to about 1 part by weight, per 100 parts by weight of the solids in the resist composition. The use of more than about 5 parts of the organic acid derivative can result in a low resolution. Depending on the combination of the other components in the resist composition, the organic acid derivative may be omitted.

Component (G): Dissolution Inhibitor

In one preferred embodiment, the resist composition further contains (G) a compound with a molecular weight of up to about 3,000 which changes its solubility in an alkaline developer under the action of an acid, e.g., a dissolution inhibitor. Typically, a compound obtained by partially or entirely substituting acid labile substituents on a phenol or carboxylic acid derivative having a molecular weight of up to about 2,500 is added as the dissolution inhibitor.

In the resist composition comprising a compound of one of formulas I-II, an appropriate amount of the dissolution inhibitor (G) is up to about 20 parts, and especially up to about 15 parts by weight per 100 parts by weight of the solids in the composition. With more than about 20 parts of the dissolution inhibitor, the resist composition becomes less heat resistant because of an increased content of monomer components.

Component (H): Alkali-Soluble Resin

Component (B), a compound of one of formulas I-II, can also be used in a chemical amplification negative-working resist composition. This composition further contains an alkali-soluble resin as component (H), examples of which are described above in the description of component (A), though the alkali-soluble resins are not limited thereto.

In various embodiments, the alkali-soluble resin can be poly(p-hydroxystyrene), partially hydrogenated p-hydroxystyrene copolymers, p-hydroxystyrene-styrene copolymers, p-hydroxystyrene-acrylic acid copolymers, and p-hydroxystyrene-methacrylic acid copolymers, a dendritic and/or hyperbranched polymer of the foregoing polymers, or combinations thereof.

The alkali-soluble resin polymer can have a weight average molecular weight (Mw) of about 3,000 to about 100,000. Many polymers with Mw of less than about 3,000 do not perform well in heat resistance and film formation. Many polymers with Mw of more than 100,000 give rise to problems with respect to dissolution in the resist solvent and developer. The polymer can have a dispersity (Mw/Mn) of up to about 3.5, and more preferably up to about 1.5. With a dispersity of more than about 3.5, resolution is sometimes lower than is desired. Although the preparation method is not critical, a poly(p-hydroxystyrene) or similar polymer with a low dispersity or narrow dispersion can be synthesized by controlled free radical or living anionic polymerization.

To impart a certain function, suitable substituent groups can be introduced into some of the phenolic hydroxyl and carboxyl groups on the acid labile group-protected polymer. Various embodiments include substituent groups for improving adhesion to the substrate, substituent groups for improving etching resistance, and especially substituent groups that are relatively stable against acid and alkali and are effective for controlling dissolution rate such that the dissolution rate in an alkali developer of unexposed and low exposed areas of a resist film does not increase to an undesirable level. Illustrative non-limiting substituent groups include 2-hydroxyethyl, 2-hydroxypropyl, methoxymethyl, methoxycarbonyl, ethoxycarbonyl, methoxycarbonylmethyl, ethoxycarbonylmethyl, 4-methyl-2-oxo-4-oxolanyl, 4-methyl-2-oxo-4-oxanyl, methyl, ethyl, n-propyl, iso-propyl, n-butyl, sec-butyl, acetyl, pivaloyl, adamantyl, isobornyl, and cyclohexyl. It is also possible to introduce acid-decomposable substituent groups such as t-butoxycarbonyl and relatively acid-undecomposable substituent groups such as t-butyl and t-butoxycarbonylmethyl.

An acid crosslinking agent capable of forming a crosslinked structure under the action of an acid is also contained in the negative resist composition. Typical acid crosslinking agents are compounds having at least two hydroxymethyl, alkoxymethyl, epoxy or vinyl ether groups in a molecule. Substituted glycoluril derivatives, urea derivatives, and hexa(methoxymethyl)melamine compounds are suitable as the acid crosslinking agent in the chemically amplified negative-resist composition comprising the photoacid generators described herein. Examples of acid crosslinking agents include N,N,N',N'-tetramethoxymethylurea, hexamethoxymethylmelamine, tetraalkoxymethyl-substituted glycoluril compounds such as tetrahydroxymethyl-substituted glycoluril and tetramethoxy-methylglycoluril, and condensates of phenolic compounds such as substituted or unsubstituted bis(hydroxymethylphenol) compounds and bisphenol A with epichlorohydrin. In certain specific embodiments, the acid crosslinking agent can be one or more of 1,3,5,7-tetraalkoxy-methylglycolurils such as 1,3,5,7-tetramethoxymethylglycoluril, 1,3,5,7-tetrahydroxymethylglycoluri-l, 2,6-dihydroxymethyl-p-cresol, 2,6-dihydroxymethylphenol, 2,2',6,6'-tetrahydroxymethyl-bisphenol A, 1,4-bis[2-(2-hydroxypropyl)]benzene, N,N,N',N'-tetramethoxymethylurea, and hexamethoxymethylmelamine. In the resist composition, an appropriate amount of the acid crosslinking agent is about 1 to about 25 parts, and especially about 5 to about 15 parts by weight per 100 parts by weight of the solids in the composition. The acid crosslinking agents may be used alone or in admixture of two or more.

Component (J): Low Molecular Weight Alkali-Soluble Compound

Component (J), an alkali-soluble compound having a molecular weight of up to about 2,500 can be blended into the chemical amplification type negative-working resist composition. The compound should preferably have at least two phenol and/or carboxyl groups. Illustrative non-limiting examples include cresol, catechol, resorcinol, pyrogallol, fluoroglycin, bis(4-hydroxyphenyl)methane, 2,2-bis(4'-hydroxyphenyl)propane, bis(4-hydroxyphenyl)sulfone, 1,1,1-tris(4'-hydroxyphenyl)ethane, 1,1,2-tris(4'-hydroxyphenyl)ethane, hydroxybenzophenone, 4-hydroxyphenylacetic acid, 3-hydroxyphenylacetic acid, 2-hydroxyphenylacetic acid, 3-(4-hydroxyphenyl)propionic acid, 3-(2-hydroxyphenyl)propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, salicylic acid, 4,4-bis(4'-hydroxyphenyl) valeric acid, 4-tert-butoxyphenylacetic acid, 4-(4-hydroxyphenyl)butyric acid, 3,4-dihydroxymandelic acid, and 4-hydroxymandelic acid. In certain specific embodiments, component (J) is salicylic acid and/or 4,4-bis(4'-hydroxyphenyl)valeric acid. The compounds can be used alone or in admixture of two or more. The addition amount can be 0 to about 20 parts, preferably about 2 to about 10 parts by weight per 100 parts by weight of the solids in the composition.

Additional Optional Components

In the resist composition according to the invention, there may be additional additives such as a surfactant for improving coating, and/or a light absorbing agent for reducing diffuse reflection from the substrate.

Illustrative non-limiting examples of the surfactant include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303 and EF352 (Tohkem Products K.K.), Megaface F171, F172 and F173 (Dai-Nippon Ink & Chemicals K.K.), Florade FC430 and FC431 (Sumitomo 3M K.K.), Asahiguard AG710, Surflon S-381, S-382, SC101, SC102, SC103, SC104, SC105, SC106, Surfynol E1004, KH-10, KH-20, KH-30 and KH-40 (Asahi Glass K.K.); organosiloxane polymers KP341, X-70-092 and X-70-093 (Shin-Etsu Chemical Co., Ltd.), acrylic acid or methacrylic acid Polyflow No. 75 and No. 95 (Kyoeisha Ushi Kagaku Kogyo K.K.). In certain specific embodiments, FC430, Surflon S-381 and Surfynol E1004 are employed. These surfactants may be used alone or in combination with others.

In the resist composition, the surfactant can be formulated in an amount of up to about 2 parts, and especially up to about 1 part by weight, per 100 parts by weight of the solids in the resist composition.

A UV absorber can be added to the resist composition. An appropriate amount of UV absorber blended is 0 to about 10 parts, more preferably about 0.5 to about 10 parts, most preferably about 1 to about 5 parts by weight per 100 parts by weight of the base resin.

For the microfabrication of integrated circuits, any well-known lithography may be used to form a resist pattern from the chemical amplification positive- or negative-working resist composition.

Substrates

The composition can be applied to a substrate (e.g., Si, $SiO_2$, SiN, SiON, TiN, WSi, BPSG, SOG, organic anti-reflecting film, etc.) by a suitable coating technique such as spin coating, roll coating, flow coating, dip coating, spray coating or doctor coating. The coating can be prebaked on a hot plate at a temperature of about 60° C. to about 150° C. for about 1 to about 10 minutes, typically about 80° C. to about 120° C. for about 1 to 5 minutes. The resulting resist film is generally about 0.1 to about 2.0 µm thick. With a mask having a desired pattern placed above the resist film, the resist film can then be exposed to actinic radiation, typically having an exposure wavelength of up to about 300 nm, such as UV, deep-UV, electron beams, x-rays, excimer laser light, γ-rays or synchrotron radiation in an exposure dose of about 1 to 200 $mJ/cm^2$, typically about 10 to 100 $mJ/cm^2$. The film can be further baked on a hot plate at about 60° C. to about 150° C. for about 1 to 5 minutes, typically about 80° C. to about 120° C. for about 1 to 3 minutes (post-exposure baking=PEB).

Thereafter the resist film can be developed with a developer in the form of an aqueous base solution, for example, about 0.1% to about 5%, typically about 2% to about 3% aqueous solution of tetramethylammonium hydroxide (TMAH) for about 0.1 to 3 minutes, typically about 0.5 to about 2 minutes by conventional techniques such as dipping, puddling, or spraying. In this way, a desired resist pattern can be formed on the substrate. It is appreciated that the resist composition of the invention is well suited for micro-patterning using such actinic radiation as deep UV with a wavelength of about 254 nm to about 193 nm, 13.4 nm (EUV), electron beams, x-rays, excimer laser light, y-rays and/or synchrotron radiation. With any of the above-described parameters outside the above-described range, the process may sometimes fail to produce the desired pattern.

General Synthetic Procedures for Photoacid Generator Compounds

The useful PAGs described herein can be prepared as outlined below in the Examples and by using techniques and reaction sequences known to those of skill in the art.

The compounds described herein can be prepared by any of the applicable techniques of organic synthesis. Many such techniques are well known in the art. However, many of the known techniques are elaborated in *Compendium of Organic Synthetic Methods* (John Wiley & Sons, New York) Vol. 1, Ian T. Harrison and Shuyen Harrison (1971); Vol. 2, Ian T. Harrison and Shuyen Harrison (1974); Vol. 3, Louis S. Hegedus and Leroy Wade (1977); Vol. 4, Leroy G. Wade Jr., (1980); Vol. 5, Leroy G. Wade Jr. (1984); and Vol. 6, Michael B. Smith; as well as March, J., *Advanced Organic Chemistry*, 3rd Edition, John Wiley & Sons, New York (1985); *Comprehensive Organic Synthesis. Selectivity, Strategy & Efficiency in Modern Organic Chemistry, In 9 Volumes*, Barry M. Trost, Editor-in-Chief, Pergamon Press, New York (1993); *Advanced Organic Chemistry, Part B: Reactions and Synthesis*, 4th Ed.; Carey and Sundberg; Kluwer Academic/Plenum Publishers: New York (2001); *Advanced Organic Chemistry, Reactions, Mechanisms, and Structure*, 2nd Edition, March, McGraw Hill (1977); *Protecting Groups in Organic Synthesis*, 2nd Edition, Greene, T. W., and Wutz, P. G. M., John Wiley & Sons, New York (1991); and *Comprehensive Organic Transformations*, 2nd Edition, Larock, R. C., John Wiley & Sons, New York (1999).

It is appreciated that those of skill in synthetic organic chemistry understand that reagents are typically referred to by the chemical names that they bear or formulae that represent their structures prior to addition to a chemical reaction mixture, even though the chemical species actually present in the reaction mixture or involved in the reaction may be otherwise. While a compound may undergo conversion to a compound bearing a different name or represented by a different formula prior to or during a specified reaction step, reference to these compounds by their original name or formula is acceptable and is well-understood by those of skill in the art of organic chemistry.

Obviously, numerous modifications and variations of the present invention are possible in light of the above teachings. It is therefore to be understood that within the scope of the appended claims, the invention may be practiced otherwise than as specifically described herein.

Specific ranges, values, and embodiments provided below are for illustration purposes only and do not otherwise limit the scope of the invention, as defined by the claims.

The following literature is incorporated herein by reference:

PAG General Reviews:

Shirai, M.; Tsunooka, M., "Photoacid and photobase generators: chemistry and applications to polymeric materials" *Progress in Polymer Science* 1996, 21(1), 1-45.

Shirai, M.; Suyama, K.; Okamura, H.; Tsunooka, M., "Development of novel photosensitive polymer systems using photoacid and photobase generators" *Journal of Photopolymer Science and Technology* 2002, 15(5), 715-730.

Nitobenzyl Core:

Houlihan, F. M.; Neenan, T. X.; Reichmanis, E.; Kometani, J. M.; Chin, T., "Design, synthesis, characterization, and use of all-organic, nonionic photogenerators of acid" *Chemistry of Materials* 1991, 3(3), 462-71.

Ahmad Hasan, Klaus-Peter Stengele, Heiner Giegrichl, Paul Cornwell, Kenneth R. Isham, Richard A. Sachleben, Wolfgang Pfleiderer, and Robert S. Foote, Photolabile Protecting Groups for Nucleosides: Synthesis and Photodeprotection Rates, *Tetrahedron*, Vol. 53, No. 12, pp. 4247-4264, 1997.

Serafinowski and Garland, *J Am. Chem. Soc.* 2003, 125, 962-965.

Imide Core:

Iwashima, C.; Imai, G.; Okamura, H.; Tsunooka, M.; Shirai, M., "Synthesis of i- and g-line sensitive photoacid generators and their application to photopolymer systems" *Journal of Photopolymer Science and Technology* 2003, 16(1), 91-96.

Okamura, Haruyuki; Sakai, Koichi; Tsunooka, Masahiro; Shirai, Masamitsu; Fujiki, Tsuyoshi; Kawasaki, Shinich; Yamada, Mitsuaki. I-line sensitive photoacid generators and their use for photocrosslinking of polysilane/diepoxyfluorene blend. Journal of Photopolymer Science and Technology (2003), 16(1), 87-90.

Okamura, Haruyuki; Sakai, Koichi; Tsunooka, Masahiro; Shirai, Masamitsu. Evaluation of quantum yields for decomposition of 1-line sensitive photoacid generators. Journal of Photopolymer Science and Technology (2003), 16(5), 701-706.

Okamura, Haruyuki; Matsumori, Ryosuke; Shirai, Masamitsu. I-line sensitive photoacid generators having thianthrene skeleton. Journal of Photopolymer Science and Technology (2004), 17(1), 131-134.

Also incorporated by reference into this disclosure are U.S. Pat. Nos. 6,316,639 (Fritz-Langhals; "Process for the preparation of cyclic N-hydroxy-dicarboximides"); 6,582,879 (Choi et al.; "Reactive photo acid-generating agent and heat-resistant photoresist composition with polyamide precursor"); 6,692,893 (Ohsawa et al.); 7,105,267 (Hatakeyama et al.); and 7,163,776 (Sasaki et al.); and U.S. Patent Application Publication No. 2005/0186505 (Kodama et al.).

The following Examples are intended to illustrate the above invention and should not be construed as to narrow its scope. One skilled in the art will readily recognize that the Examples suggest many other ways in which the present invention could be practiced. It should be understood that many variations and modifications may be made while remaining within the scope of the invention.

EXAMPLES

The variable groups defined in the following Examples are for illustrative purposes, and the embodiments described in the Examples are not limited to those values in other embodiments. Certain groups, ranges, and specific variables that can be employed in the various embodiments are further described above in the summary and detailed description.

Example 1

General Synthesis of an Ionic Photoacid Generator

Ionic photoacid generators according to various embodiments can be prepared as illustrated below in Scheme 1-1.

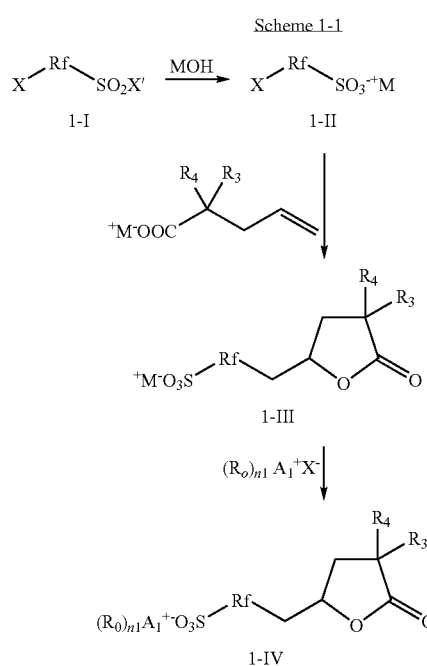

Scheme 1-1

The synthetic procedure to prepare ionic photoacid generator (1-IV) with a perfluorooxyalkyl group which is in turn attached to lactone ring via an alkyl linkage is summarized below. Reaction of halogen containing perfluorooxyalkyl sulfonyhalide (1-I) with alkali metal hydroxide results in perfluorooxyalkylsulfonate (1-II). Compound 1-III was obtained by reacting 1-II with the sodium salt of an alkenoic acid in the presence of dehalogeno-alkylating reagents. Finally an exchange reaction of sulfonate (1-III) with a photoactive cation in an aqueous or aqueous/organic solvent system affords new ionic photoacid generator 1-IV, wherein the variables are as defined in the Summary above.

See Hu and Qing, *J. Org. Chem*, 1991, 56, 6348-6351; Zou et al., *Tetrahedron*, 2003, 59, 2555-2560; Imazeki et al., *Synthesis*, 2004, 10, 1648-1654; and Crivello and Lam, *Macromolecules*, 1977, 10, 1307-1315 for related synthetic techniques and procedures.

Certain specific examples of ionic PAGs include compounds I-1 through 1-2, including the various stereoisomers of compounds 1-3 and 1-4:

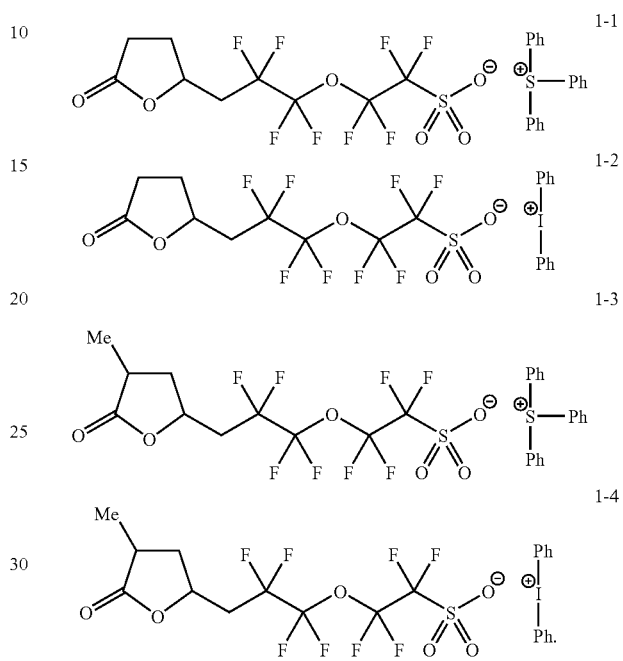

The methyl group of compounds 1-3 and 1-4 provides advantageous properties the PAGs including increased melting points and crystallinity. Compounds 1-1 and 1-2 tend to be oils and not crystalline solids.

Thermal and optical properties of iodonium PAG 1-2 and various comparative PAGs are shown below in Table 1.

TABLE 1

Thermal and Optical Properties

| PAG | Acid size[a] (cm$^3$) | $T_d$ (° C.) | $T_m$ (° C.) | $\epsilon_{248}$[b] (cm$^2 \cdot$ mol$^{-1}$) |
|---|---|---|---|---|
| Cl–(CH$_2$)$_2$(CF$_2$)$_2$–SO$_3$$^-$Ph$_2$I$^+$ | 146 | 205 | 154 | NA |
| Ph–O–(CF$_2$)$_2$–SO$_3$$^-$Ph$_2$I$^+$ | 241 | 190 | 134 | 6015 |
| Norbornyl–(CF$_2$)$_2$–O–(CF$_2$)$_2$–SO$_3$$^-$Ph$_2$I$^+$ | 240 | 164 | 104 | 5220 |

TABLE 1-continued

Thermal and Optical Properties

| PAG | Acid size[a] (cm³) | $T_d$ (°C.) | $T_m$ (°C.) | $\epsilon_{248}$[b] (cm²·mol⁻¹) |
|---|---|---|---|---|
| 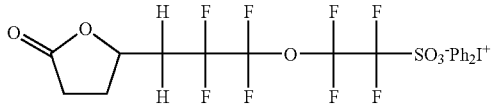 | 232 | 165 | −20[c] | 5400 |
| 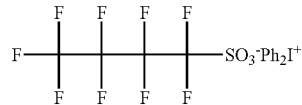 | 162 | NA | 78 | 4200 |
| 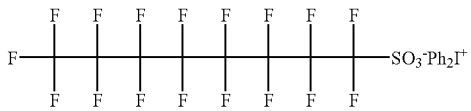 | 272 | NA | NA | NA |

[a]Estimated by ACD lab software;
[b]Measured in acetonitrile;
[c]Transparent oil at room temperatures (23° C.).

Other comparative data of PAG properties are shown in Table 2.

TABLE 2

PAG Property Comparisons

| | Sulfonate Anion | Acid | Acid Molar Volume (cm³) | $M_W$ | Sulfonate Anion F wt % | Sulfonate Anion H wt % |
|---|---|---|---|---|---|---|
| PFOS | 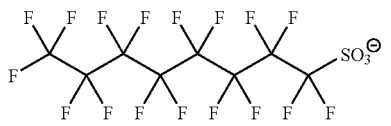 |  | 272.1 | 500.13 | 64.58 | — |
| PFBuS | 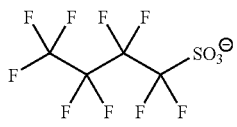 |  | 162.3 | 300.10 | 59.98 | — |
| norbornyl- | 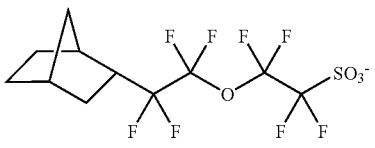 |  | 240.0 | 392.26 | 38.85 | 2.83 |
| lactone- | 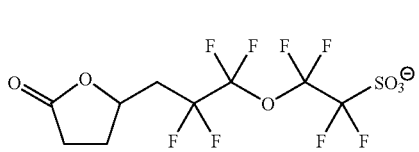 |  | 232.0 | 396.21 | 38.46 | 1.79 |

Other useful PAGs include compounds of formula X:

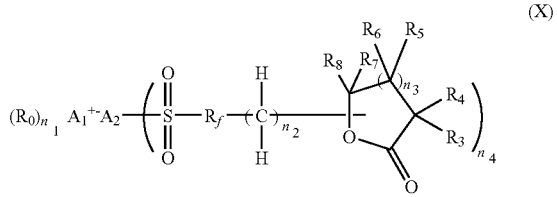

wherein $R_f$ is a diradical carbon chain comprising one to about 20 carbon atoms wherein the chain can be optionally interrupted by one to five oxygen atoms, and each carbon atom is substituted with zero to two halo groups, typically two fluoro groups;

each of $R_3$-$R_8$ is independently H, alkyl, cycloalkyl, heterocycle, aryl, or heteroaryl;

$n_2$ is 0, 1, 2, 3, 4, or 5;

$n_3$ is 1 or 2;

$A_1$ is I or S and when $A_1$ is I, then $n_1$ is 2 and when $A_1$ is S, then $n_1$ is 3;

each Ro is independently alkyl, cycloalkyl, heterocycle, aryl, or heteroaryl, each optionally substituted with one to about five substituents; and $A_2$ is O and $n_4$ is 1, or $A_2$ is N and $n_4$ is 2.

As is readily understood by one skilled in the art, the chain that includes the fluorinated carbons can be attached to the lactone group at any viable position on the lactone ring. In various embodiments, $R_f$ can be fluorinated alkyl groups optionally interrupted by oxygen atoms, for example —CF$_2$CF$_2$—O—CF$_2$CF$_2$— or —(CF$_2$)$_m$ wherein m is 1 to about 10 (or 1 to about 8, or 1 to about 6). The lactone ring can optionally have one cite of unsaturation.

Still other useful PAGs include compounds of formula XI:

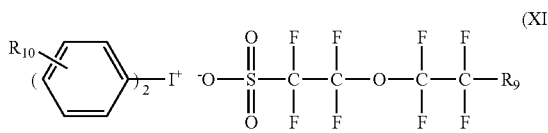

wherein $R_9$ can be L-R* wherein L can be —CH$_2$—, —NH—, or —O—; R* can be alkyl, cycloalkyl, cycloalkoxy, alkoxy, heterocycle, aryl, heteroaryl; and $R_{10}$ can be H, alkyl, or acyloxy. In various embodiments, the heterocycle is a cycloether. In other embodiments, the cycloalkyl is norbornyl or adamanty. In certain embodiments, $R_{10}$ is tbutyl or an alkyl ester, for example, methyl carboxylate.

Example 2

Synthesis of an Ionic Photoacid Generator

Ionic photoacid generators according to various embodiments can be prepared as illustrated below in Scheme 2-1.

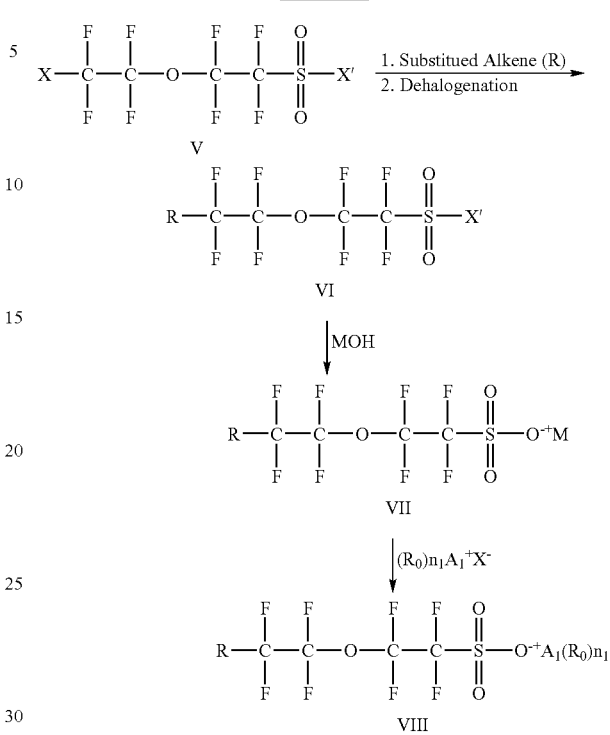

Ionic photoacid generator VIII with a perfluorooxyalkyl group directly attached to an alkyl or cycloalkyl group can be synthesized as illustrated above wherein X and X' are halo, R is alkyl, cycloalkyl, heterocycle, aryl, or heteroaryl, each optionally substituted with one to about five substituents. Sulfonyl halide V (commercially available or synthesized in one to about five steps) can be converted to compound VI by reacting with a substituted alkene in the presence of dehalogeno-alkylating reagents. Compound VI was converted to sulfonate VII by direct oxidation with an alkali metal hydroxide, for example, NaOH or KOH. The resulting sulfonate obtained was then subjected to an exchange reaction with a photoactive cation in an aqueous or an aqueous/organic solvent system to afford new ionic photoacid generator VIII, wherein $A_1$ is iodonium or sulfonium, each (Ro) is independently alkyl, cycloalkyl, heterocycle, aryl, or heteroaryl, each optionally substituted with one to about five substituents, and $n_1$ is 2 or 3.

See Feiring and Wonchoba, *Journal of Fluorine Chemistry*, 2000, 105, 129; De Vleeschauwer and Gauthier, *Synlet,* 1997, 375-377; Blonty, *Tetrahedron Letters,* 2003, 44, 1499-1501; Feiring, *Journal of Organic Chemistry,* 1985, 50, 3269-3274; Hu and Qing, *J. Org. Chem,* 1991, 56, 6348-6351; and Crivello and Lam, *Macromolecules,* 1977, 10, 1307-1315 for related synthetic techniques and procedures.

Example 3

General Synthesis of an Ionic Photoacid Generator

Ionic photoacid generators according to various embodiments can be prepared as illustrated below in Scheme 3-1.

Scheme 3-1

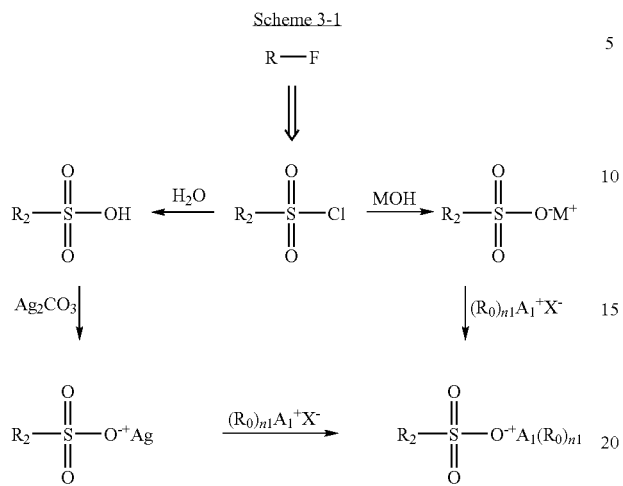

A simplified synthetic procedure to obtain an ionic photoacid generator with a perfluoro or aryl group directly attached to the sulfonate group is described below. A sulfonyl chloride (commercially available or synthesized in one to about five steps) was converted to sulfonate either by direct oxidation with an alkali metal hydroxide or by hydrolysis followed by neutralization with silver carbonate. The sulfonate obtained was then subjected to an exchange reaction with a photoactive cation in an aqueous or an aqueous/organic solvent system to afford a new ionic photoacid generator, wherein $R_2$ can be alkyl, cycloalkyl, heterocycle, aryl, or heteroaryl, each optionally substituted with one to about five substituents, and $A_1$, (Ro), $n_1$ can be defined as in Example 2.

See Feiring and Wonchoba, *Journal of Fluorine Chemistry,* 2000, 105, 129; Vleeschauwer and Gauthier, *Synlet,* 1997, 375-377; Blonty, *Tetrahedron Letters,* 2003, 44, 1499-1501; Houlihan et al., F. M.; *Chemistry of Materials* 1991, 3 (3), 462-71; Hu and Qing, *J Org Chem,* 1991, 56, 6348-6351; and Crivello and Lam, *Macromolecules,* 1977, 10, 1307-1315 for related synthetic techniques and procedures.

Example 4

Synthesis of Non-Ionic Photoacid Generators

Nonionic photoacid generators according to various embodiments can be prepared as illustrated below in Scheme 4-1.

Scheme 4-1

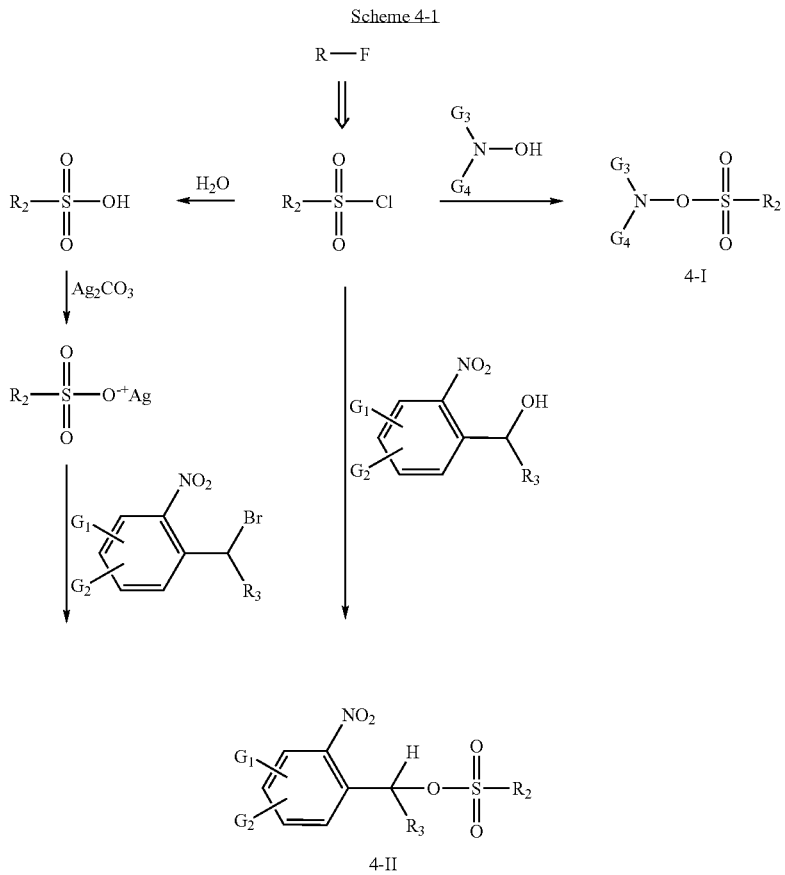

A sulfonyl chloride (commercially available or synthesized from the corresponding precursors) can be used to prepare nonionic PAGs. The imide based PAGs 4-I were prepared by reaction of the corresponding N-hydroxyimide with an appropriate sulfonyl chloride in the presence of a base. A nitrobenzyl PAG 4-II can be synthesized either by reacting a silver sulfonate with nitrobenzyl bromide or by reacting a nitrobenzyl alcohol with a sulfonyl chloride in the presence of coupling reagents.

In various embodiments, $R_2$, $R_3$, $G_1$, $G_2$, $G_3$ and $G_4$ can each independently be alkyl, cycloalkyl, heterocycle, aryl, or heteroaryl, each optionally substituted with one to about five substituents. For example, in certain embodiments $R_2$ can be $(C_1-C_8)$alkyl, or phenyl, each optionally substituted, for example, with one to five substituents. In certain embodiments, $R_3$ can be H or $(C_1-C_6)$alkyl. In certain embodiments, $G_1$ and $G_2$ can be H, halo, alkyl, alkoxy, carboxy, cyano, acyl, acyloxy, trifluoromethyl, amino, or nitro. In certain embodiments, $G_3$ and $G_4$ can each independently be H, $(C_1-C_8)$alkyl, acyl, aroyl, or a nitrogen protecting group; or, $G_3$ and $G_4$ can form a heteroaryl or heterocycle group together with the nitrogen atom to which they are attached.

See Feiring and Wonchoba, *J. Fluorine Chemistry*, 2000, 105, 129; De Vleeschauwer and Gauthier, *Synlet*, 1997, 375-377; Blonty, *Tetrahedron Lett*, 2003, 44, 1499-1501; Iwashima et al., *J. Photopolymer Science and Technology* 2003, 16 (1), 91-96; Okamura et al., *J. Photopolymer Science and Technology* 2003, 16 (1), 87-90; Okamura et al., *J. Photopolymer Science and Technology* 2003, 16 (5), 701-706; Okamura et al., *J. Photopolymer Science and Technology* 2004, 17 (1), 131-134; Houlihan et al., *Chemistry of Materials* 1991, 3 (3), 462-71 for related synthetic techniques and procedures.

Various nonionic PAGs can be prepared as illustrated in Scheme 4-2 below.

Scheme 4-2

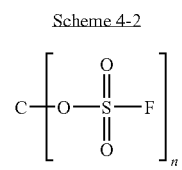

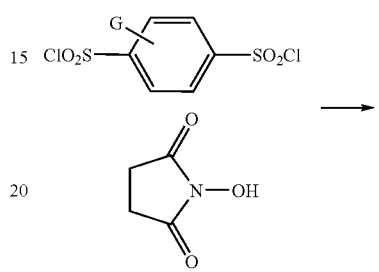

wherein G is H, halo, nitro, amino, alkyl, alkoxy, cycloalkyl, heterocycle, aryl, or heteroaryl; and wherein one to about five hydrogen atoms on a given G group can be optionally substituted.

Various other nonionic PAGs can be prepared as illustrated in Schemes 4-3 and 4-4:

Scheme 4-3

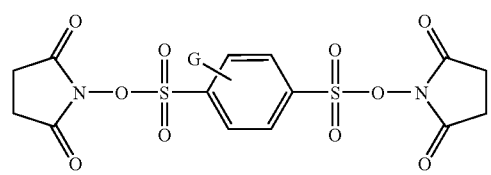

C = Non-metallic photosensitive chromophore (FIG. 2)
F = Same (FIG. 3)
where n = 1 or 2

For Example If n = 1 and F

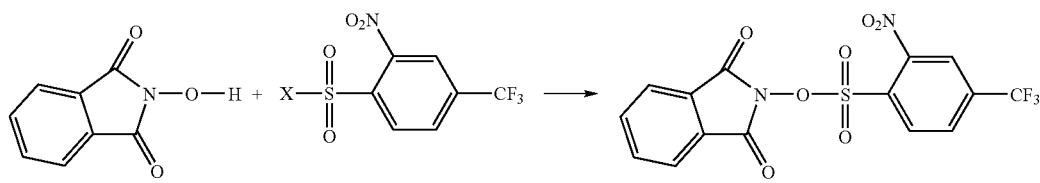

For Example If n = 2 and F
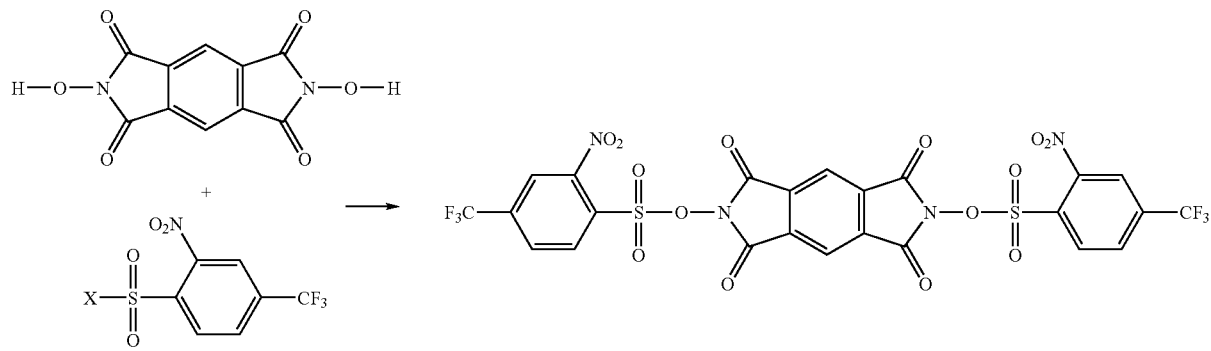
Scheme 4-4
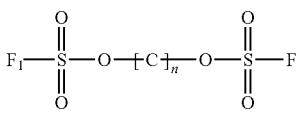
C = Non-metallic photosensitive chromophore (FIG. 2)
F and $F_1$ = Same or different fluoroorganic group (FIG. 3)
where n = 1 or 2
For Example If n = 1 and F = F and F = 1
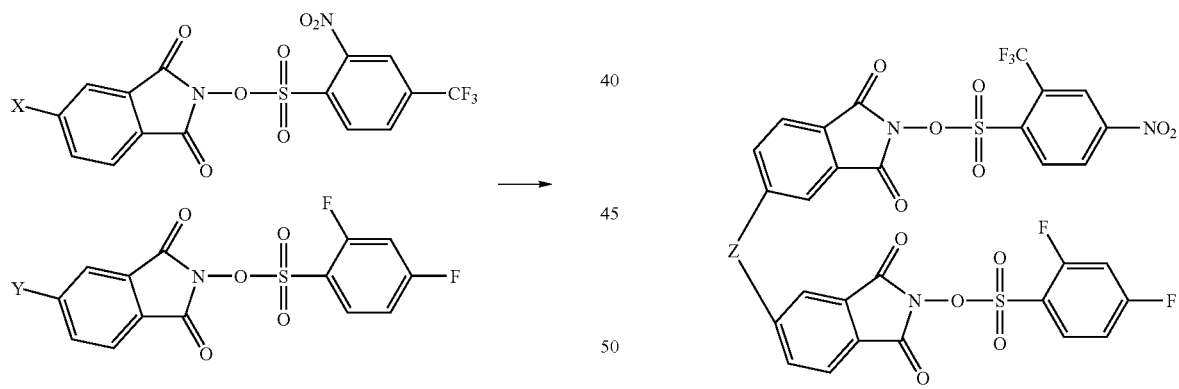
For Example If n = 2 and F = F and F 1
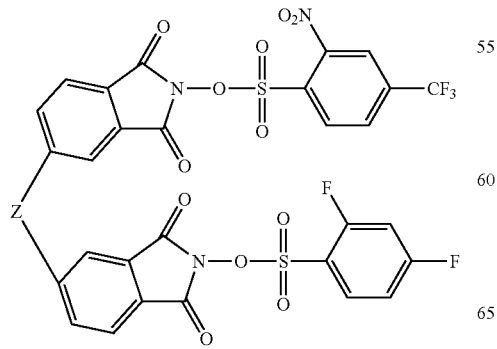
Other nonionic PAGs include the compounds of Scheme 4-5 and phenyl substitution stereoisomeric derivatives thereof.
Scheme 4-5
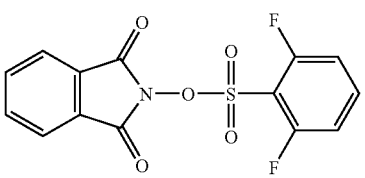

-continued

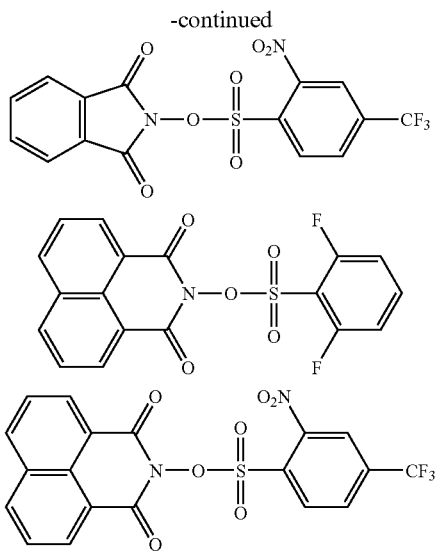

Example 5

Nonionic Photoacid Generating Compounds with Functionalized Fluoroorganic Sulfonate Motif Photoacid generators (PAG) improve sensitivity and offer flexibility in designing chemically amplified resist (CAR) systems. Acid generating efficiency (acid generation mechanism, physico-chemical properties and lithography performance) is strongly dependent on PAG structures. Nonionic photoacid generators (PAGs) with an appropriate combination of photosensitive chromophore and photoacid generating motif are of great interest because they offer a wider range of absorption, lithographic performance, solubility, and thermal properties than many widely used ionic PAGs. Any nonionic PAG that is expected to be viable in commercial applications, including lithographic techniques, should be free of perfluorooctyl sulfonate (PFOS) because of the environmental concerns associated with PFOS PAGs. The nonionic photoacid generators described herein can be photosensitive fluoroorganic sulfonic esters of amides, imides, nitrobenzyl groups, and their derivatives (e.g., these groups substituted with one to five substituents, which are described above in the Detailed Description). Generic examples are illustrated below in Scheme 5-1. Initial photosensitive chromophores and fluoroorganic groups useful for preparing nonionic PAGs of Scheme 5-1 are shown in Schemes 5-2 and 5-3.

Scheme 5-1.
Generic structures of environmentally friendly Nonionic PAGs.

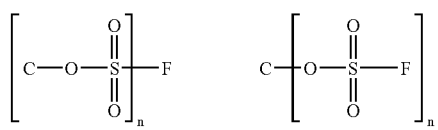

-continued

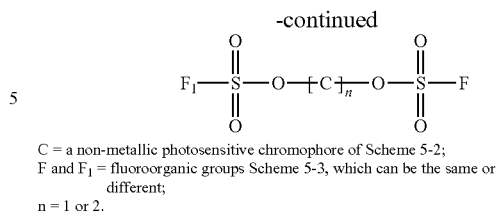

C = a non-metallic photosensitive chromophore of Scheme 5-2;
F and $F_1$ = fluoroorganic groups Scheme 5-3, which can be the same or different;
n = 1 or 2.

Scheme 5-2.
Photosensitive chromophores (C) and their derivatives

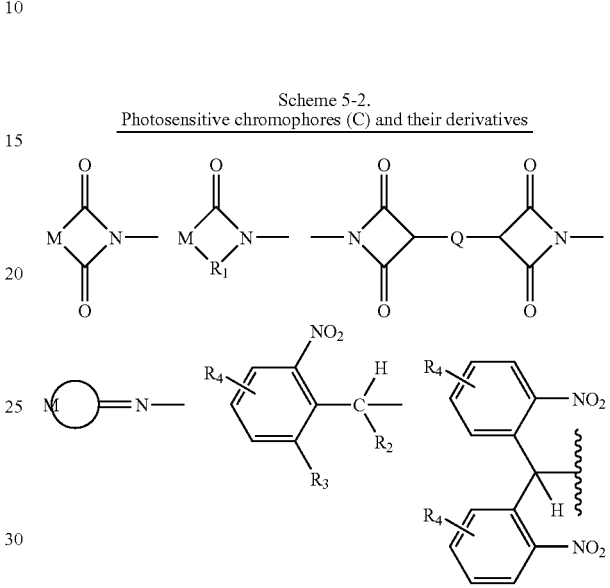

wherein
M=a non-metallic atom that is a member of one or more rings that contain 2 to about 16 other ring atoms, which may include heteroatoms (e.g., N or O), and which may optionally possess one to about five substituents;
$R_1$-$R_4$=H, halo, nitro, amino, alkyl, alkoxy, cycloalkyl, heterocycle, aryl, or heteroaryl;
Q=aryl optionally substituted with one to about five substituents.

In certain embodiments, $R_2$ is H, methyl, phenyl, or methoxyphenyl (any one of ortho-, meta-, or para-). In various embodiments, $R_3$ is H, nitro, F, or trifluoromethyl. In various embodiments, $R_4$ can be H, methoxy, dimethylamino, nitro, or bromo.

Scheme 5-3.
Fluoroorganic (F) groups and their derivatives for nonionic PAGs

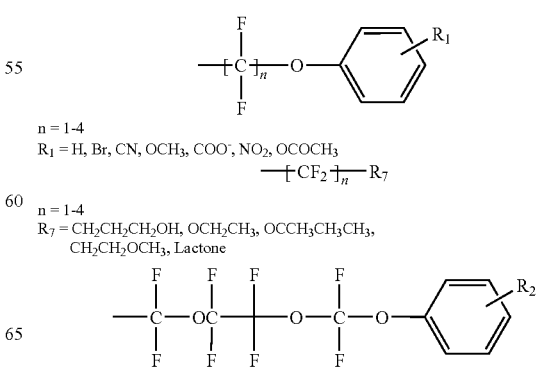

n = 1-4
$R_1$ = H, Br, CN, $OCH_3$, $COO^-$, $NO_2$, $OCOCH_3$ n = 1-4
$R_7$ = $CH_2CH_2CH_2OH$, $OCH_2CH_3$, $OCCH_3CH_3CH_3$, $CH_2CH_2OCH_3$, Lactone -continued R$_2$ = H, Br, CN, OCH$_3$, COO$^-$, NO$_2$, OCOCH$_3$

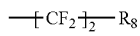

R$_8$ = Cl, CH$_2$CH$_2$Cl, CH=CH$_2$

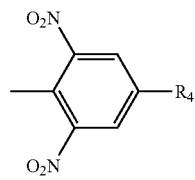

R$_4$ = H, F, Br, OCH$_3$, COO$^-$, CN, OCOCH$_3$

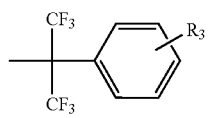

R$_3$ = H, F, Cl, CH$_3$

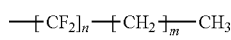

m = 1-6, n = 1-4

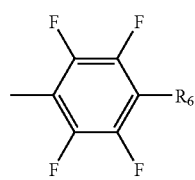

R$_6$ = H, F, Br, OCH$_3$, COO$^-$, CN, OCOCH$_3$

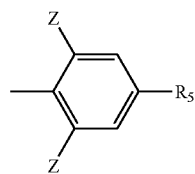

Z = F or CF$_3$;
R$_5$ = H, F, CF$_3$

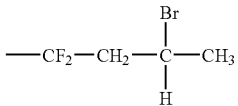

Several reports have been documented concerning developing nonionic PAGs with improved physico-chemical properties. However, most reports concentrate on the chromophore to alter their absorption range or the thermal properties of the nonionic PAGs. A design disclosed in this Example focuses on improving sensitivity and lithography performance of the nonionic PAGs. A photoacid group can be employed, which is a combination of partially, semi-, or unfluorinated sulfonate with functional groups. The acidity and miscibility of the PAG can be altered by functional groups or a combination of reduced number of fluorine atoms with functional groups that in turn improve the sensitivity of the PAG as well as its distribution in the polymer matrix. The functional groups selected can help to reduce particle formation in solution and can increase uniform detect-free, thin film formation.

In order to reduce the outgassing/contamination and photoacid diffusion, a photoacid group or photosensitive groups can be anchored to flexible/rigid oligomeric molecules. To further improve the sensitivity and lithographic performance, nonionic PAGs with multiple or two different photoacid structures are being developed. In addition to photoacid structure design, the absorption and thermal properties of the PAG can be controlled by taking advantage of various substituent effects and symmetry of the structures. These nonionic PAGs are non-metallic in nature and can produce sulfonic acids that contain reduced amount of fluorine and functional groups upon irradiation. These PAGs are environmentally friendly, as well as semiconductor process friendly. Their lithographic performances are enhanced compared to conventional PAGs because the functionalized groups are incorporated into the nonionic PAGs, which improves several properties of these PAGs, including solubility, sensitivity, and optical properties.

Example 6

Photoacid Generators (PAGs) Based on Novel Fluorinated Groups

Chemically amplified resist (CAR) materials containing photoacid generators (PAGs) have facilitated the semiconductor manufacturing process from 250 nm to 90 nm. Even in 193 nm and next generation lithography (NGL), it is also viable to fabricate the continuingly decreased feature size of microelectronics. Among the CAR system, photoacid generator (PAG) is a critical component. It generates acid once absorbing a photon and then catalyzes numerous chemical reactions in the exposed area of the resist film. Resist sensitivity or the photospeed is thus increased dramatically (100 wafers/hour). PAGs based on ionic and non-ionic molecules were developed. Both of them are composed of two parts, the acid precursor and the chromophore. The chemical structure of PAG has great impact on the resist performances. For example, if a PAG is not homogeneously distributed in the resist film, it will lead to patterning profile problems such as T-topping, footing and skin formation. Acid diffusion is another important issue. In order to minimize the line width roughness (LWR), photoacid should have suitable size to control the acid diffusion rate. Moreover, as the feature size decreases in NGL, the contribution to patterning properties from PAG becomes more and more significant. If a PAG is not carefully selected, it will result in patterning deviation and the poor device performances. Besides the technical problems discussed above, PAGs should be practically non-toxic and friendly to environment. In order to tackle the technical and safety issues, a series of ionic and nonionic PAGs having novel functionalized acid precursors has been designed. The target chemicals are revealed in this patent application. The structures of certain specific and general ionic PAGs are listed in FIG. 2 and the structures of certain specific and general nonionic PAGs are listed in FIG. 3.

An effective way to improve the resist performances and sensitivity is to develop new PAGs having novel chemical structures. Based on the modular design approach, functional groups were introduced into perfluorinated acid precursors to control the acid size and volatility while maintaining the acid strength. The functional groups for acid precursors were selected to mimic the groups in the resist side chain so that the PAG interacts with resist and distribute uniformly. The photo generated acid is then able to diffuse at an optimum level.

For example, because 193 nm and EUV resist include γ-lactone and benzene side groups, PAGs having lactone or aromatic groups are able to distribute uniformly in the polymer matrix, which leads to lower variation in the resulting lithographic patternings. Furthermore, the presence of strong PAG/polymer interaction reduces leaching levels of these PAGs when they are used in 193 immersion lithography.

These PAGs have good solubility in organic solvents widely used in microlithography, such as PGMEA, γ-butyrolactone and ethyl lactate. The PAGs are thermally stable as most of NGL requires high activation energy resist. The thermal and absorption properties of the PAGs can be controlled by balancing the composition of element. The designed PAGs can be used not only in semiconductor manufacturing but also in various coating applications. It is important that any PAG developed should be non-toxic and environmentally friendly. In contrast to PFOS-based PAGs, the PAG structures listed in this application contain significantly reduced amounts of fluorine and are therefore less toxic to the environment and human health.

All literature and patent citations above are hereby expressly incorporated by reference at the locations of their citation. Specifically cited sections or pages of the above cited works are incorporated by reference with specificity. The invention has been described in detail sufficient to allow one of ordinary skill in the art to make and use the subject matter of the following Embodiments. It is apparent that certain modifications of the methods and compositions of the following Embodiments can be made within the scope and spirit of the invention.

What is claimed is:

1. A compound of formula I:

$$\left( (R_o)_{\overline{n_1}} A_1^{\oplus} \right) \quad A_2^{\ominus} \left( \underset{O}{\overset{O}{\underset{\|}{S}}} R_f \left( \underset{}{} \right)_{n_3} \underset{O}{\underset{\bigcirc}{\bigcirc}} (R^1)_{n_5} \right)_{n_2}$$
(I)

wherein
- $A_1$ is I or S;
- $n_1$ is 2 when $A_1$ is I, and $n_1$ is 3 when $A_1$ is S;
- each Ro is independently alkyl, cycloalkyl, heterocycle, aryl, or heteroaryl, each optionally substituted with one to about five substituents;
- $A_2$ is O or N;
- $n_2$ is 1 when $A_2$ is O and $n_2$ is 2 when $A_2$ is N;
- $R_f$ is a diradical carbon chain comprising one to about 20 carbon atoms wherein the chain is optionally interrupted by one to five oxygen atoms, and each carbon atom is substituted with zero to two halo groups, or $R_f$ is a direct bond;
- each $R_1$ is independently H, alkyl, cycloalkyl, heterocycle, aryl, or heteroaryl;
- $n_3$ is 0 to about 10;
- $n_4$ is 1 or 2;
- $n_5$ is 0 to 7; and
- any aryl or heteroaryl of formula I is optionally substituted with one to five halo, $(C_1-C_6)$alkyl, alkoxy, acyl, alkoxycarbonyl, alkoxyacyl, acyloxy, trifluoromethyl, trifluoromethoxy, hydroxy, cyano, carboxy, nitro, or $—N(R^2)_2$ groups;
- any alkyl, cycloalkyl, heterocycle, aryl, or heteroaryl is optionally substituted with one to five halo, $(C_1-C_6)$alkyl, alkoxy, acyl, alkoxyacyl, acyloxy, trifluoromethyl, trifluoromethoxy, hydroxy, cyano, carboxy, nitro, $—N(R^2)_2$, or oxo groups; and
- each $R^2$ is independently H, alkyl, aryl, acyl, or aroyl.

2. The compound of claim 1 wherein Ro is aryl or heteroaryl.

3. The compound of claim 1 wherein at least one carbon of $R_f$ is substituted with two fluoro groups or $R_f$ is a direct bond.

4. The compound of claim 1 wherein $R_f$ is $—(CF_2)_n—$ wherein n is 1 to about 6, $—C(CF_3)_2—$, $—(CF_2)—O—(CF_2)_2—O—(CF_2)—$, $—(CF_2)_2—O—(CF_2)_2—$, or a direct bond.

5. The compound of claim 1 wherein $n_3$ is 1; $n_4$ is 1; and $n_5$ is 0.

6. The compound of claim 1 wherein $n_5$ is 1 and $R^1$ is $(C_1-C_8)$alkyl.

7. The compound of claim 1 wherein $n_5$ is 1 and $R^1$ is methyl.

8. The compound of claim 1 wherein the compound is $(Ph)_3S^+ \ ^-OSO_2—CF_2CF_2—O—CF_2CF_2—CH_2—$[lactone], $(Ph)_2I^+ \ ^-OSO_2—CF_2CF_2—O—CF_2CF_2—CH_2—$[lactone], $(Ph)_3S^+ \ ^-OSO_2—CF_2CF_2—O—CF_2CF_2—CH_2—$[methyl lactone], or $(Ph)_2I^+ \ ^-OSO_2—CF_2CF_2—O—CF_2CF_2—CH_2—$[methyl lactone].

9. The compound of claim 1 wherein the compound is a photoacid generator.

10. A chemical amplification type resist composition comprising the photoacid generator of claim 9, a resin, and a solvent system.

11. A composition comprising a compound of claim 9 and a resin that changes its solubility in an alkaline developer when contacted with an acid.

12. A composition comprising a compound of claim 9 and a compound that is capable of generating an acid upon exposure to radiation and that is not a compound of claim 9.

13. The composition of claim 10 further comprising a basic compound.

14. A method to form a pattern comprising:
 a) applying onto a substrate a resist composition comprising a compound of claim 9, to provide a substrate with a coating;
 b) heat treating the coating and exposing the coating to high energy radiation or electron beam through a photomask; and
 c) optionally heat treating the exposed coating and developing the coating with a developer.

* * * * *

UNITED STATES PATENT AND TRADEMARK OFFICE
CERTIFICATE OF CORRECTION

| | |
|---|---|
| PATENT NO. | : 7,824,839 B2 |
| APPLICATION NO. | : 12/255266 |
| DATED | : November 2, 2010 |
| INVENTOR(S) | : Christopher K. Ober et al. |

It is certified that error appears in the above-identified patent and that said Letters Patent is hereby corrected as shown below:

Title page 2, under "Other Publications", in column 2, line 4, delete "Perfluoroalkylk" and insert -- Perfluoroalkyl --, therefor.

Title page 2, under "Other Publications", in column 2, line 9, delete "1-Chlor-" and insert -- 1-Chloro- --, therefor.

Title page 2, under "Other Publications", in column 2, line 31, delete "Propargy" and insert -- Propargyl --, therefor.

Title page 2, under "Other Publications", in column 2, line 32, delete "3-(Perfluoroalky)" and insert -- 3-(Perfluoroalkyl) --, therefor.

In column 2, line 14-15, delete "non-bioaccumalitive" and insert -- non-bioaccumulative --, therefor.

In column 8, line 32, delete "1H-indazoly," and insert -- 1H-indazolyl, --, therefor.

In column 8, line 66, delete "1-azetedyl," and insert -- 1-azetidyl, --, therefor.

In column 17, line 65, delete "Nitobenzyl" and insert -- Nitrobenzyl --, therefor.

In column 18, line 28, delete "1-line" and insert -- I-line --, therefor.

In column 19, lines 32-33, delete "sulfonyhalide" and insert -- sulfonylhalide --, therefor.

In column 20, line 6, delete "I-1" and insert -- 1-1 --, therefor.

In column 20, line 38, delete "the" and insert -- of the --, therefor.

In column 23, line 28, delete "Ro" and insert -- $R_0$ --, therefor.

Signed and Sealed this
First Day of February, 2011

David J. Kappos
*Director of the United States Patent and Trademark Office*

CERTIFICATE OF CORRECTION (continued)
U.S. Pat. No. 7,824,839 B2

In column 24, line 49, delete "(Ro)" and insert -- ($R_0$) --, therefor.

In column 26, line 11, delete "(Ro)," and insert -- ($R_0$), --, therefor.

In column 26, line 16, delete "J Org" and insert -- J. Org. --, therefor.

In column 30, line 22, delete "F 1" and insert -- F=1 --, therefor.

In column 32, line 65, delete " " and insert -- 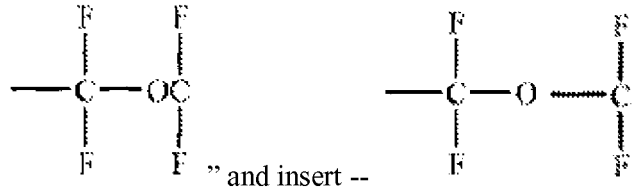 --, therefor.

In column 35, line 38, in Claim 1, delete "Ro" and insert -- $R_0$ --, therefor.

In column 35, line 48, in Claim 1, delete "$R_1$" and insert -- $R^1$ --, therefor.

In column 36, line 4, in Claim 2, delete "Ro" and insert -- $R_0$ --, therefor.